United States Patent
Morita et al.

(10) Patent No.: US 9,977,043 B2
(45) Date of Patent: May 22, 2018

(54) METHOD OF SUPPLYING REAGENT TO MICROCHIP, MICROCHIP, AND DEVICE FOR SUPPLYING REAGENT TO MICROCHIP

(71) Applicant: USHIO DENKI KABUSHIKI KAISHA, Tokyo (JP)

(72) Inventors: Kinichi Morita, Tokyo (JP); Toshikazu Kawaguchi, Sapporo (JP); Katsuaki Shimazu, Sapporo (JP)

(73) Assignee: USHIO DENKI KABUSHIKI KAISHA, Tokyo (JP)

(*) Notice: Subject to any disclaimer, the term of this patent is extended or adjusted under 35 U.S.C. 154(b) by 80 days.

(21) Appl. No.: 14/402,652

(22) PCT Filed: May 14, 2013

(86) PCT No.: PCT/JP2013/063362
§ 371 (c)(1),
(2) Date: Nov. 20, 2014

(87) PCT Pub. No.: WO2013/175996
PCT Pub. Date: Nov. 28, 2013

(65) Prior Publication Data
US 2015/0153371 A1    Jun. 4, 2015

(30) Foreign Application Priority Data
May 22, 2012 (JP) .................. 2012-116367

(51) Int. Cl.
| | | |
|---|---|---|
| *B01L 3/00* | (2006.01) | |
| *G01N 35/10* | (2006.01) | |
| *G01N 33/531* | (2006.01) | |

(52) U.S. Cl.
CPC .... *G01N 35/1095* (2013.01); *B01L 3/502715* (2013.01); *G01N 33/531* (2013.01);
(Continued)

(58) Field of Classification Search
CPC .............. G01N 35/1095; G01N 33/531; B01L 3/502715; B01L 2200/027;
(Continued)

(56) References Cited

U.S. PATENT DOCUMENTS

| | | | |
|---|---|---|---|
| 2003/0062067 A1* | 4/2003 | Meyer ..................... | B01L 9/523 134/25.4 |
| 2004/0037739 A1* | 2/2004 | McNeely .................. | B01F 5/10 422/417 |

(Continued)

FOREIGN PATENT DOCUMENTS

| | | |
|---|---|---|
| JP | 3714338 B2 | 9/2005 |
| JP | 2006-187730 A | 7/2006 |
| JP | 2011-220996 A | 11/2011 |

OTHER PUBLICATIONS

International Search Report; PCT/JP2013/063362; dated Jun. 18, 2013.

*Primary Examiner* — Erik B Crawford
(74) *Attorney, Agent, or Firm* — Studebaker & Brackett PC

(57) ABSTRACT

A microchip includes a reagent placement area to fix an anaerobic antibody therein. An inlet and outlet of the microchip that communicate with a channel having the reagent placement area are closed by thin plate sections and a sealing member. The sealing member is made from a silicone gel and possesses a self-repairing capability. To supply the reagent to the microchip, a fluid releasing unit having an aperture and a fluid recovering unit having an aperture are caused to penetrate the thin plate sections and the self-repairable sealing element, and enter a space including the reagent placement area. The free end of the fluid releasing unit is shaped like an injection needle, and the aperture serves as a fluid release opening. The free end of the fluid (Continued)

recovering unit is shaped like an injection needle, and the aperture serves as a fluid recovery opening.

12 Claims, 14 Drawing Sheets

(52) U.S. Cl.
CPC . *B01L 2200/027* (2013.01); *B01L 2200/0689* (2013.01); *B01L 2200/16* (2013.01); *B01L 2300/044* (2013.01); *B01L 2300/0636* (2013.01); *B01L 2300/0816* (2013.01); *B01L 2300/0819* (2013.01); *B01L 2300/0877* (2013.01); *B01L 2400/0487* (2013.01); *B01L 2400/0683* (2013.01); *Y10T 436/25* (2015.01); *Y10T 436/2575* (2015.01)

(58) Field of Classification Search
CPC ......... B01L 2200/0689; B01L 2200/16; B01L 2300/044; B01L 2300/0636; B01L 2300/0816; B01L 2300/0819; B01L 2300/0877; B01L 2400/0487; B01L 2400/0683; Y10T 436/25; Y10T 436/2575
See application file for complete search history.

(56) References Cited

U.S. PATENT DOCUMENTS

| | | | |
|---|---|---|---|
| 2004/0116686 A1* | 6/2004 | Akashi | B01L 3/50273 536/25.4 |
| 2004/0211511 A1 | 10/2004 | Suzuki | |
| 2006/0032746 A1* | 2/2006 | Knott | B01J 19/0093 204/450 |
| 2007/0149863 A1* | 6/2007 | Padmanabhan | B01L 3/502715 600/309 |
| 2009/0023202 A1* | 1/2009 | Narahara | G01N 21/6428 435/287.9 |
| 2012/0315191 A1 | 12/2012 | Maekawa et al. | |

* cited by examiner

A-A CROSS SECTION

A-A CROSS SECTION

FIG. 13

METHOD OF SUPPLYING REAGENT TO MICROCHIP, MICROCHIP, AND DEVICE FOR SUPPLYING REAGENT TO MICROCHIP

TECHNICAL FIELD

The present invention relates to a method of supplying a reagent to a microchip used to, for example, separate (isolate), synthesize (compose), extract (sample), and/or analyze a trace amount of reagent. The present invention also relates to a microchip used for such method, and a reagent supplying device for supplying the reagent to the microchip.

BACKGROUND ART

In recent years, a micro-scale analysis channel or the like is formed on a small base plate (substrate), which is made from, for example, a silicon, silicone, glass or other materials, by a semiconductor microfabrication (fine processing) technology to provide a microchip. Such microchip is used as a microreactor to, for example, separate (isolate), synthesize (compose), extract (sample), and/or analyze a trace amount of reagent. Examples of microchip and methods of fabricating the microchip are disclosed in, for example, Patent Literature 1 (Japanese Patent Application Laid-Open Publication No. 2006-187730) and Patent Literature 2 (Japanese Patent No. 3714338).

The microchip has a channel or flow channel, which is often referred to as a microchannel. This channel includes a plurality of areas having prescribed functions respectively, such as a reaction area in which a reagent is placed. Accordingly, the microchips can be configured to suit for various applications. Typical applications of the microchip include analyses in the fields of chemistry, biology, pharmacy, medical science, and veterinary medicine (e.g., genetic analysis, clinical diagnosis, and drug screening), and also include composition synthesis as well as environmental measurement (monitoring).

Typically, the microchip has a pair of base plates that face each other and are bonded to each other, and also has a fine channel formed in the surface of at least one of the base plates. For example, the fine channel is 10 to several hundred μm in width and 10 to several hundred μm in depth. Conventional microchips generally use glass base plates because the glass base plates are easy to fabricate and are optically detectable. Recently developed microchips use resin base plates because the resin base plates are light in weight, difficult to break (as compared with the glass base plates), and inexpensive.

In the field of medical science, the microchip is used for measurements in the clinical (laboratory) test or the like when the measurements take advantage of intermolecular interaction such as immune reaction. Such measurements include, for example, the surface plasmon resonance (SPR) measurement, the quartz crystal microbalance (QCM) measurement, and the functional (functionalized) surface-based measurement. The functional surface is made from a material (e.g., from colloidal gold particle to ultrafine particle). Such microchip has an antibody that is fixed in, for example, the channel in advance. A reagent, which contains an antigen, is caused to flow in the channel such that an antibody-antigen reaction takes place. Measurements about the antibody-antigen reaction are carried out with the microchip.

FIG. 9(a) of the accompanying drawings schematically illustrates a microchip 10. FIG. 9(b) illustrates a cross-sectional view taken along the A-A line in FIG. 9(a). As shown in FIG. 9(a), the microchip 10 includes a pair of base plates (first microchip base plate 11 and a second microchip base plate 12) which face each other and are bonded to each other. The microchip 10 also includes a fine channel 14 that has an inlet 13a and an outlet 13b. The channel 14 is, for example, 10 to several hundred μm in width and 10 to several hundred μm in depth. Specifically, as shown in FIG. 9(b), the channel 14 is defined by a fine groove formed in the first microchip base plate 11, and the upper surface of the second microchip base plate 12. A metallic thin film 15 is disposed in the channel 14. The metallic thin film 15 is located on the upper surface of the second microchip base plate 12 in the channel (i.e., the bonding surface between the first and second base plates 11 and 12). The metallic thin film 15 includes a chrome (Cr) thin film and a gold (Au) thin film laminated on the chrome thin film.

Fixing the antibody in the channel 14 of the microchip is carried out by, for example, the following manner.

As shown in FIG. 10(a) of the accompanying drawings, a reagent solution feeding tube (filling pipe) 101 is fitted in the inlet 13a of the microchip 10. Likewise, a reagent solution discharge tube 102 is fitted in the outlet 13b of the microchip 10. A joint element 103 is attached to a free end of the reagent solution feeding tube 101, and another joint element 103 is attached to a free end of the reagent solution discharge tube 102. These joint elements 103 are connected to the inlet 13a and the outlet 13b, respectively.

Phosphate buffered saline (referred to as "PBS" hereinafter) is fed to the channel 14 of the microchip 10 from the reagent solution feeding tube 101 to clean the channel 14. The PBS that flows through the channel 14 is discharged to the outside from the reagent solution discharge tube 102, which is connected to the outlet 13b of the channel 14.

Referring next to FIG. 10(b), a solution to make an ASM (e.g., alkanthiol-containing solution) is fed to the channel 14 of the microchip 10 from the reagent solution feeding tube 101. Alkanthiol contained in the alkanthiol-containing solution reacts with the Au thin film, and an SAM film (Self-Assembled Monolayer film) 16 is formed on the Au thin film. The alkanthiol-containing solution that does not contribute to the formation of the SAM film is discharged to the outside through the reagent solution discharge tube 102.

Subsequently, as shown in FIG. 10(c), the PBS is fed to the channel 14 of the microchip 10 from the reagent solution feeding tube 101 to remove the remaining alkanthiol-containing solution from the channel 14. The PBS that flows through the channel 14 is discharged to the outside from the reagent solution discharge tube 102.

Then, as shown in FIG. 11(d) of the accompanying drawings, an antibody-containing solution is fed to the channel 14 of the microchip 10 from the reagent solution feeding tube 101. The antibody contained in the antibody-containing solution reacts with the alkanthiol SAM film 16 and chemically bonds to the alkanthiol SAM film 16 such that the antibody is fixed (secured) on the SAM film 16. Thus, the antibody Ig is fixed on the metallic thin film 15.

Because the floating antibody may remain on the surface of the antibody Ig fixed on the SAM film 16 and/or the antibody may stay in an area other than the SAM film 16 in the channel 14, the PBS is fed to the channel 14 of the microchip 10 from the reagent solution feeding tube 101, as shown in FIG. 11(e), to purge the remaining antibody with the PBS. The PBS that contains the residual antibody is discharged to the outside from the reagent solution discharge tube 102 that is connected to the outlet 13b of the channel 14.

In general, the antibody becomes inactive (deactivated) when the antibody contacts the air. Thus, after the residual antibody is purged with the PBS, the interior of the channel 14 is filled with the PBS, as shown in FIG. 11(f), to avoid the contact with the air. The inlet 13a and the outlet 13b of the microchip 10 are sealed by sealing members 104 (e.g., paraffin film or the like), respectively.

LISTING OF REFERENCES

Patent Literatures

PATENT LITERATURE 1: Japanese Patent Application Laid-Open Publication No. 2006-187730
PATENT LITERATURE 2: Japanese Patent No. 3714338

SUMMARY OF THE INVENTION

Problems to be Solved

As shown in FIG. 9(b), the channel of the microchip 10 often bends at right angles near the inlet 13a and the outlet 13b. When the antibody-containing solution is forced to flow in such channel 14, a turbulent flow occurs in the antibody-containing solution that flows in the channel 14. Because of the turbulent flow, as shown in FIG. 12, the contact between the antibody contained in the antibody-containing solution and the alkanthiol SAM film 16 becomes disordered. This impedes (hinders) the reaction between the antibody and the SAM film 16, and therefore it becomes difficult to fix (hold) the antibody on the SAM film 16.

Also, when the reagent solution feeding tube 101 and the reagent solution discharge tube 102 are detached from the channel 14 of the microchip 10, and the joint elements 103 mounted on the free ends of the reagent solution feeding tube 101 and the reagent solution discharge tube 102 are removed from the inlet 13a and the outlet 13b, respectively, as shown in FIG. 13, then bubbles are often generated at the inlet 13a and the outlet 13b.

Likewise, when the sealing members 104 that seal the inlet 13a and the outlet 13b of the microchip 10, such as paraffin films, are removed respectively prior to feeding the antigen-containing reagent toward the antibody fixed in the channel 14, as shown in FIG. 14, bubbles are often generated at the inlet 13a and the outlet 13b.

When the reagent solution feeding tube 101 and the reagent solution discharge tube 102 are attached to the microchip channel 14 to feed the antigen-containing reagent into the channel 14, and the joint elements provided at the free ends of the reagent solution feeding tube 101 and the reagent solution discharge tube 102 are joined to the inlet 13a and the outlet 13b respectively, then bubbles are often generated at the inlet 13a and the outlet 13b.

When the bubbles are generated in the channel 14, and the reagent solution and other matters are discharged from the channel 14, then the bubbles move in the channel 14, and the bubbles contact the antibody. In such case, the antibody contacts the air and therefore certain types of antibody become inactive.

As such, when the conventional microchip 10 is used to cause the antibody-containing solution to flow in the channel 14 and fix the antibody in the channel 14, the turbulent flow generated in the channel 14 makes it difficult to fix the antibody in the channel 14.

When the reagent solution feeding tube 101 and the reagent solution discharge tube 102 are attached or detached in order to feed the reagent in the channel 14, and/or when the sealing members 104 are removed from the inlet 13a and the outlet 13b of the channel 14 in order to temporarily keep the microchip 10 at a different place, the bubbles are easily generated in the channel 14. Thus, when the antibody is fixed in the channel 14, the antibody may become inactive.

The present invention was developed in view of the above-described facts, and an object of the present invention is to provide a method of supplying a reagent to a microchip, which has a reagent placement area, to stably supply an anaerobic reagent, such as anaerobic antibody, to the microchip without irregularities and with almost no contact between the reagent placement area of the microchip and the air. The reagent placement area is an area to fix the anaerobic antibody. Another object of the present invention is to provide a microchip used in such method.

Still another object of the present invention is to provide an apparatus for supplying a reagent to a microchip, which can supply an anaerobic reagent, such as an anaerobic antibody, to a reagent placement area of the microchip with almost no contact with the air.

Solution to the Problems

In order to solve the above-described problems, one aspect of the present invention provides a microchip that includes a channel in the form of a space having a reagent placement area therein and also includes an inlet and an outlet which communicates with the channel. The inlet and the outlet are airtightly closed by a silicone gel having a self-repairing (self-restoring) capability.

A fluid releasing unit having a free end, which is shaped like an injection needle and has an opening as a fluid release opening, and a fluid recovering unit having a similar shape to the fluid releasing unit penetrate the silicone gel disposed over the inlet and the outlet respectively and enter the space including the reagent placement area. The reagent such as an anaerobic antibody is supplied to the channel, which is the reagent placement area, from the opening of the fluid releasing unit, and the reagent supplied to the channel is recovered from the opening of the fluid recovering unit.

As a result, it is possible to supply the reagent such as the anaerobic antibody to the reagent placement area and recover the reagent from the reagent placement area with almost no contact with the air.

It should be noted that the silicone gel is difficult to mold with the metal molds, and therefore a recess (step portion) may be formed around the inlet and the outlet or at a different position, and the silicone gel may be poured in the recess (step portion) to close the inlet and the outlet (will be described). In this case, it is preferred that the inlet and the outlet are closed by, for example, thin plate members in order to prevent the silicone gel from flowing in the channel when the silicone gel is poured to close the inlet and the outlet.

Preferably, the thin plate members have a thickness that allows the fluid releasing unit and the fluid recovering unit to easily penetrate. For example, when the inlet and the outlet are formed, the inlet and the outlet may be closed by thin plate sections that are integral with a member of the microchip.

The reagent supplying apparatus for supplying the reagent to the microchip includes the fluid releasing unit, the fluid recovering unit, and a unit configured to allow the fluid releasing unit and the fluid recovering unit to penetrate the silicone gel having the self-repairing capability and enter the space including the reagent placement area and to allow the fluid releasing unit and the fluid recovering unit to be removed from the space including the reagent placement area.

Because the reagent supplying apparatus has the above-described configuration, it is possible to stably, without irregularities, supply the reagent such as the anaerobic antibody to the reagent placement area of the microchip and recover the reagent from the reagent placement area with almost no contact with the air.

In summary, the present invention overcomes the above-described problems in the following manner.

(1) The microchip includes the channel in the form of the space having the reagent placement area therein. The microchip also includes the inlet and the outlet which serve as the openings of the channel. The inlet and the outlet are airtightly closed by the silicone gel that has the self-repairing capability. The reagent is supplied to the microchip in the following manner.

First Step: A fluid releasing unit having a free end, which is shaped like an injection needle, and having an opening as a fluid release opening, and a fluid recovering unit having a free end, which is shaped like an injection needle, and having an opening as a fluid recovery opening, are caused to penetrate the silicone gel disposed at the inlet and the outlet respectively and enter the space including the reagent placement area. Thus, the opening of the fluid releasing unit and the opening of the fluid recovering unit are communicated with the space including the reagent placement area.

Second Step: The reagent is fed from the fluid releasing unit, and the reagent is discharged from the fluid recovering unit. Thus, the reagent is supplied to the space of the reagent placement area.

Third Step: After supplying the reagent, the fluid releasing unit and the fluid recovering unit are removed from the silicone gel.

(2) In the method of supplying the reagent according to the above-described aspect (1), a plurality of kinds of reagent may be successively fed to the channel having the reagent placement area of the microchip from the fluid releasing unit. The reagents which are successively fed to the channel may be discharged by the fluid recovering unit.

The plural kinds of reagents may include an anaerobic antibody-containing solution, which will be fixed in (on) the reagent placement area. The reagent may be fed such that the liquid level of the reagent reaches a height that completely immerses the anaerobic antibody fixed in the reagent placement area.

(3) A microchip to which the reagent is supplied in accordance with the method of the above-described aspect (1) or (2) is configured as follows.

The microchip includes a channel in the form of the space having a reagent placement area therein. The microchip also includes openings which serve as an inlet and an outlet to communicate with the channel. The inlet and the outlet, i.e., the openings of the channel, are airtightly closed by a silicone gel that has a self-repairing capability.

(4) A reagent supplying apparatus configured to supply a reagent to a channel of a microchip is configured as follows. The microchip includes the channel in the form of the space having a reagent placement area therein. The microchip also includes an inlet and an outlet which serve as the openings of the channel. The inlet and the outlet of the channel are airtightly closed by a silicone gel that has a self-repairing function (self-repairing capability).

The reagent supplying apparatus includes a fluid releasing unit configured to release (introduce) the reagent to the channel, and a fluid recovering unit configured to discharge the reagent from the channel. Each of the fluid releasing unit and the fluid recovering unit includes a hollow cylindrical member, and a free end of such hollow cylindrical member is closed. The free end of the hollow cylindrical member is shaped like an injection needle. An opening is formed in the cylindrical side wall of the hollow cylindrical member that allows fluid communication with the inner hollow of the hollow cylindrical member.

Each of the fluid releasing unit and the fluid recovering unit penetrates a silicone gel having a self-repairing capability that closes the openings of the microchip (i.e., the inlet and the outlet of the microchip). The openings of the fluid releasing unit and the fluid recovering unit reach the space of the channel and communicate with the space of the channel. The openings of the fluid releasing unit and the fluid recovering unit can leave (be removed from) the space of the channel.

(5) In the reagent supplying apparatus of the above-described aspect (4), the fluid recovering unit may successively feed a plurality of kinds of reagent to the channel of the microchip, which has the reagent placement area, from the inlet of the channel. The fluid recovering unit may discharge the reagents, which are successively fed to the channel, from the outlet of the channel.

The plural kinds of reagent may include an anaerobic antibody-containing solution that will be fixed in the reagent placement area.

The opening of the fluid releasing unit may face the opening of the fluid recovering unit. The position of the lower end of the opening of the fluid recovering unit is set such that the liquid level of the reagent supplied to the channel becomes a height that completely immerses the anaerobic antibody fixed in the reagent placement area.

Advantageous Effects of the Invention

The present invention has the following advantageous effects.

(1) The microchip includes the channel in the form of the (inner) space having the reagent placement area therein. The microchip also includes the inlet and the outlet which communicate with the channel. Because the inlet and the outlet are airtightly closed by the silicone gel that has the self-repairing (self-restoring) capability, and the fluid releasing unit and fluid recovering unit have the free ends respectively, which are shaped like the injection needles, have the openings to serve as the fluid release openings, and penetrate the silicone gel disposed at the inlet and the outlet to reach the channel inner space that has the reagent placement area, it is possible to supply the anaerobic reagent such as the anaerobic antibody to the reagent placement area and to recover the reagent from the reagent placement area with almost no contact with the air.

Also, unlike the conventional technology, it is not necessary to attach the reagent solution feeding tube and the reagent solution discharge tube. Therefore, it is possible to prevent bubbles from being generated in the channel.

(2) The silicone gel that closes the inlet and the outlet has the self-repairing function, deforms upon application of a force, and returns to an original shape (shape before application of the force) upon release of the applied force. Thus, even when the fluid releasing unit and the fluid recovering unit penetrate the silicone gel and enter the reagent placement area, the close contact at the interfaces between the silicone gel and the fluid releasing unit and between the silicone gel and the fluid recovering unit is maintained favorably. Therefore, it is possible to prevent the outside air from entering the closed space (i.e., reagent placement area) from the interfaces.

(3) When the reagents which are successively supplied to the channel contain the anaerobic antibody-containing solution, the reagent is fed such that the liquid level of the reagent takes (reaches) a height that completely immerses the anaerobic antibody fixed in the reagent placement area. Thus, it is possible to prevent the anaerobic antibody from contacting the air.

(4) The reagent supplying apparatus for supplying a reagent to a microchip is provided. The microchip has the openings that serve as the inlet and the outlet, and these openings are closed by the silicone gel having the self-repairing function. The reagent supplying apparatus includes the fluid releasing unit and the fluid recovering unit. The fluid releasing unit has a hollow cylindrical member, and the free end of the fluid releasing unit is closed. The free end of the fluid releasing unit is shaped like the injection needle, and an opening is formed in the cylindrical side wall of the hollow cylindrical member to communicate with the inner hollow of the hollow cylindrical member. The fluid recovering unit has a similar shape to the fluid releasing unit. The fluid releasing unit and the fluid recovering unit penetrate the silicone gel, and enter the inner space of the microchip that has the reagent placement area. The fluid releasing unit and the fluid recovering unit can be removed from the space of the microchip. Use of such reagent supplying apparatus can substantively avoid the contact with the air and stably, without irregularities, supply the anaerobic reagent such as the anaerobic antibody to the reagent placement area of the microchip and recover the reagent from the reagent placement area.

(5) In the reagent supplying apparatus according to the above-described aspect (4), the opening of the fluid releasing unit and the opening of the fluid recovering unit may face each other. This allows the reagent supplied from the fluid releasing unit to smoothly flow through the channel of the microchip and be recovered through the opening of the fluid recovering unit. This suppresses the occurrence of the turbulent flow in the reagent flowing through the channel.

In addition, because the position of the lower end of the opening of the fluid recovering unit is set such that the liquid level of the reagent supplied to the channel becomes the height that completely immerses the anaerobic antibody fixed in the reagent placement area, it is possible to prevent the anaerobic antibody from contacting the air.

BRIEF DESCRIPTION OF THE DRAWINGS

Figure 13:
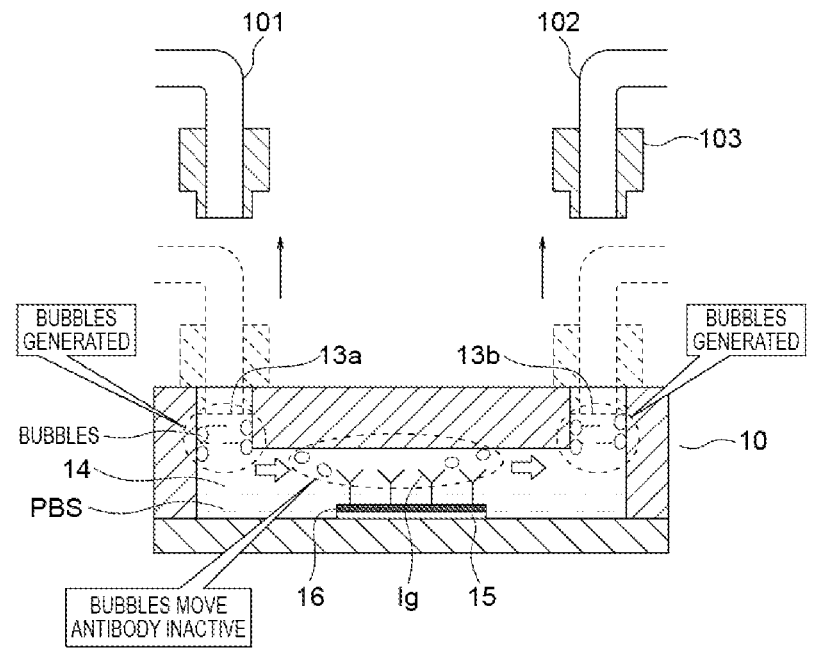

FIG. 13 is a view useful to describe how bubbles are generated when a reagent solution feeding tube and a reagent solution discharging tube are removed.

DETAILED DESCRIPTION OF THE INVENTION

FIG. 1 is a set of views illustrating a structure of a microchip having a reagent placement area according to one embodiment of the present invention.

Figure 1A:
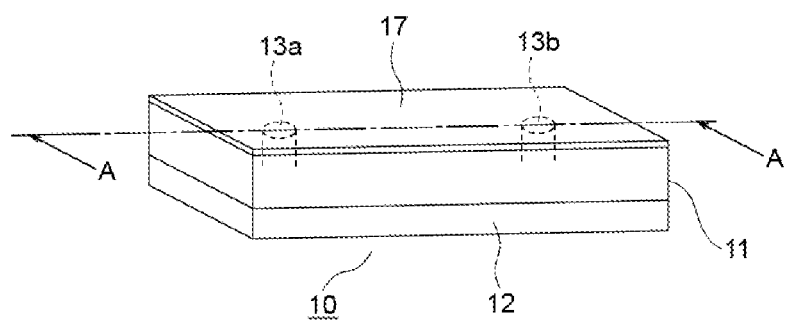
FIG. 1(a) is a perspective view showing a structure of a microchip according to an embodiment of the present invention.
Figure 1B:
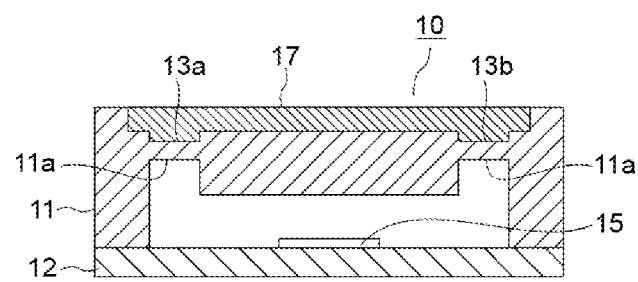
FIG. 1(b) is a cross-sectional view taken along the line A-A in FIG. 1(a).

Specifically, FIG. 1(a) shows an appearance of the microchip of this embodiment, and FIG. 1(b) shows a cross-sectional view taken along the A-A line in FIG. 1(a).

As shown in FIG. 1, the microchip 10 of this embodiment includes a pair of base plates or substrates (first microchip base plate 11 and a second microchip base plate 12). These two base plates 11 and 12 face each other, and are joined to each other. The first microchip base plate 11 is a base plate made from a silicone resin, which contains, for example, PDMS (Polydimethylsiloxane), and the second microchip base plate 12 is a base plate made from glass.

The microchip 10 includes a fine channel 14 that has an inlet 13a and an outlet 13b. The channel 14 is, for example, 10 to several hundred μm in width and 10 to several hundred μm in depth. Specifically, the channel 14 is defined by a fine groove formed in the first microchip base plate 11 and the upper surface of the second microchip base plate 12. A metallic thin film 15 is disposed in the channel 14. The metallic thin film is located on the upper surface of the second microchip base plate 12 in the channel 14 (i.e., the interface between the first and second microchip base plates 11 and 12). The metallic thin film 15 includes a chrome (Cr) thin film and a gold (Au) thin film laminated on the chrome thin film.

The microchip of this embodiment also includes thin plate sections 11a and 11a that close the inlet 13a and the outlet 13b of the channel 14 respectively. The thin plate element 11a is equal to or smaller than 100 μm in thickness. The microchip also includes a self-repairable (self-restorable) sealing member 17 on the upper surface of the first microchip base plate 11. The self-repairable sealing member 17 is made from a material that deforms upon application of a force and returns to its original shape (shape before application of the force) upon release of the force. For example, the material of the self-repairable sealing member is a silicone gel which is an adhesive gel.

In this particular embodiment, a silicone adhesive agent X-40-3331-2, which is Shin-Etsu Silicone manufactured by Shin-Etsu Chemical Co., Ltd. in Japan, was used as the silicone gel. In the following description, the structure that has the inlet 13a and the outlet 13b closed by the self-repairable sealing member 17 is referred to as the microchip 10.

Referring now to FIGS. 2 and 3, an exemplary method of manufacturing the microchip of this embodiment will be described.

The first microchip base plate 11 is a silicone resin base plate, which is made from, for example, the silicone resin X-32 (Shin-Etsu Silicone) manufactured by Shin-Etsu Chemical Co., Ltd, and the second microchip base plate 12 is a glass base plate.

Figure 2A:
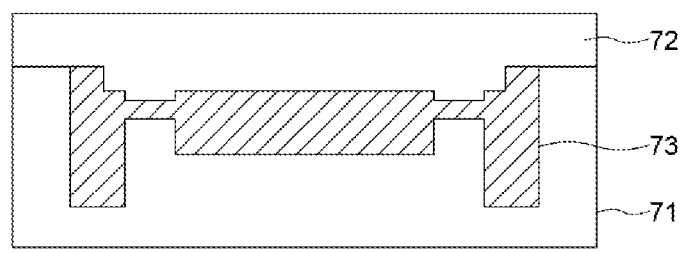
FIG. 2(a) to FIG. 2(c) are a first set of views useful to describe a method of manufacturing the microchip according to the embodiment of the present invention.

As shown in FIG. 2(a), the silicone resin (X-32) is molded by a first metal mold 71 and a second metal mold 72, and the first microchip base plate 11 is prepared.

Figure 2B:
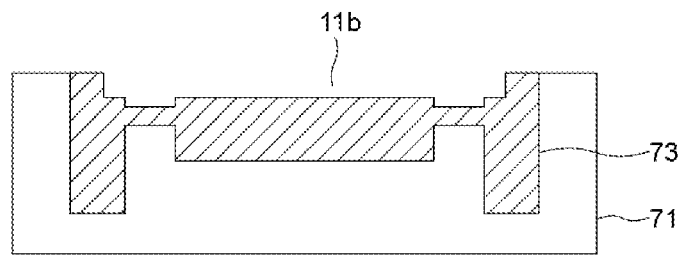

Then, as shown in FIG. 2(b), the silicone resin 73 is solidified, and the second mold 72 is removed.

Figure 2C:
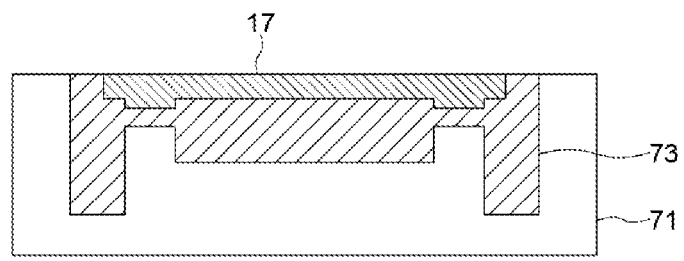

Subsequently, as shown in FIG. 2(c), an adhesive gel (e.g., Shin-Etsu Silicone X-40-3331-2 manufactured by Shin-Etsu Chemical Co., Ltd.) 17 is poured in a step portion (concave-convex portion) or recess 11b formed in the upper surface of the silicone resin 73. Then, the adhesive gel 17 and the silicone resin 73 (e.g., Shin-Etsu Silicone X-32) are united by a hot shaping (thermoforming) process.

The adhesive gel has high adhesiveness. When the metal molds are used, the metal molds adhere to the adhesive gel and the metal molds cannot be removed. In other words, it is difficult to carry out the injection molding with the metal molds.

In this embodiment, therefore, the silicone resin base plate 73 itself is used instead of the mold(s) to mold (form) the adhesive gel.

Figure 3D:
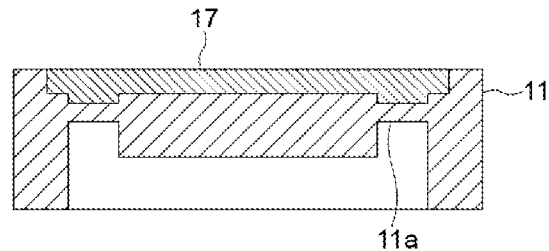
FIG. 3(d) to FIG. 3(f) are a second set of views useful to describe the method of manufacturing the microchip according to the embodiment of the present invention.

Referring next to FIG. 3(d), the hot shaping process is performed to join the adhesive gel 17 with the silicone resin 73, and then the first mold 71 is removed. The first microchip base plate 11 that has the self-repairable sealing member 17 at the top is obtained. The self-repairable sealing member is made from the adhesive gel (silicone gel).

Figure 3E:
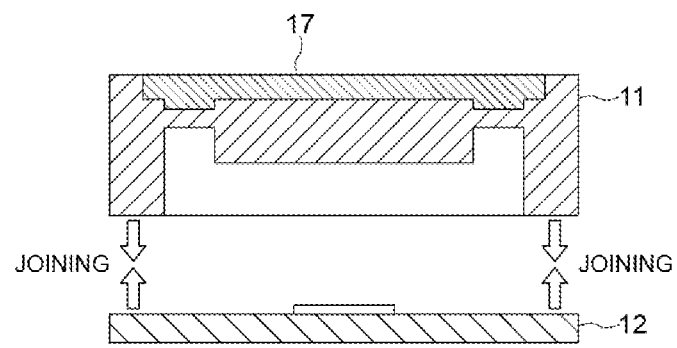
Figure 3F:
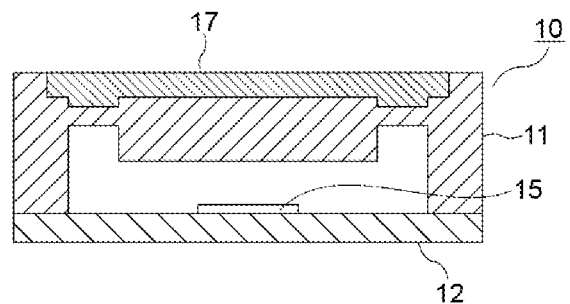

Subsequently, as shown in FIG. 3(e), the first microchip base plate 11 that has the self-repairable sealing member 17 at the top is joined to the second microchip base plate 12, which is the glass substrate. This provides the microchip 10 of this embodiment, as shown in FIG. 3(f) or FIG. 1(b).

The process for joining the first microchip base plate 11 with the second microchip base plate 12 is performed in a manner disclosed in, for example, Patent Literature 2 (Japanese Patent No. 3714338). Specifically, those surfaces of the two microchip base plates which are to be joined with each other are irradiated with a ultraviolet beam at a wavelength equal to or less than 220 nm (e.g., a ultraviolet beam emitted from a xenon excimer lamp and having a center wavelength (dominant wavelength) at 172 nm), and the surfaces irradiated with the ultraviolet beam are firmly joined with each other.

Accordingly, the self-repairable sealing member 17 is placed on the step portion 11b (placed in the recess 11b) formed in the upper portion of the first microchip base plate 11, which has the fine groove, and joined integrally. The first microchip base plate 11 that integrally has the self-repairable sealing member is joined with the second microchip base plate 12, such that the microchip 10 having the channel 14 therein is provided. In this manner, the microchip of this embodiment is prepared.

In the microchip of this embodiment shown in FIG. 1(b), the inlet 13a and the outlet 13b of the channel 14 are closed by the thin plate sections 11a which are equal to or less than 100 μm in thickness. This is because the adhesive gel (self-repairable sealing member 17) would flow in the channel 14 (space for flow) if there were no thin plate sections 11a when the adhesive gel (X-40-3331-2) is poured in the recess (step portion) 11b formed in the upper surface of the silicone resin in FIG. 2(c).

As will be described, when injection needle-shaped fluid releasing unit and injection needle-shaped fluid recovering unit of the reagent supplying apparatus penetrate the self-repairable sealing member 17 and enter the reagent placement area, the injection needle-shaped fluid releasing unit and the injection needle-shaped fluid recovering unit can easily penetrate the thin plate sections 11a because the thickness of the thin plate elements 11a is small (equal to or less than 100 μm).

In the microchip of this embodiment shown in FIG. 1, the reagent placement area that can hold the anaerobic reagent such as the anaerobic antibody is the channel inner space (inner space of the channel). Specifically, the area defined in the channel 14 (reagent placement area) is the area of the metallic thin film 15.

As described above, the microchip 10 of this embodiment has a structure that includes the inlet 13a and the outlet 13b of the channel 14 sealed by the self-repairable sealing member 17 made from, for example, a silicone gel. In other words, the microchip 10 of this embodiment has a configuration that includes the self-repairable sealing member 17 to close (seal) the reagent placement area (channel inner space). Therefore, it is possible to prevent the outside air from entering the closed space.

When the injection needle-like fluid releasing unit and the injection needle-like fluid recovering unit of the reagent supplying apparatus (will be described later) penetrate the thin plate sections 11a and the self-repairable sealing member 17 of the microchip, and enter the reagent placement area, the close contact between the self-repairable sealing member 17, the injection needle-like fluid releasing unit, and the injection needle-like fluid recovering unit is favorably maintained at the respective interfaces because the self-repairable sealing member 17 possesses a capability of deforming upon application of a force and returning to the original shape (shape before the force is applied) upon release of the applied force. Thus, the air hardly enters the reagent placement area, which is the closed space, from the outside through the interfaces of the self-repairable sealing member 17, the injection needle-like fluid releasing unit, and the injection needle-like fluid recovering unit.

Even if the injection needle-like fluid releasing unit and the injection needle-like fluid recovering unit of the reagent supplying apparatus (will be described later) are removed from (taken out) after the injection needle-like fluid releasing unit and the injection needle-like fluid recovering unit penetrate the thin plate sections 11a and the self-repairable sealing member 17 of the microchip, the self-repairable sealing member 17 deforms upon application of a force and returns to the original shape upon release of the applied force, and therefore the openings created in the self-repairable sealing member 17 by the injection needle-like fluid releasing unit and the injection needle-like fluid recovering unit that penetrate and leave (are removed from) the self-repairable sealing member 17 are promptly closed. Thus, even after the injection needle-like fluid releasing unit and the injection needle-like fluid recovering unit are removed from the self-repairable (self-repairing) sealing member 17, it is still possible to prevent the outside air from entering the reagent placement area (i.e., closed space).

Accordingly, when the injection needle-like fluid releasing unit and the injection needle-like fluid recovering unit of the reagent supplying apparatus (will be described later) are used to fix the anaerobic reagent, such as the anaerobic antibody, in the reagent placement area, the air remaining in the reagent placement area (closed space) is purged with the reagent solution or the like by the injection needle-like fluid releasing unit and the injection needle-like fluid recovering unit. This enables the anaerobic reagent (e.g., the anaerobic antibody) to be disposed in the reagent placement area with almost no contact with the air.

Now, an example of the reagent supplying apparatus configured to supply the anaerobic reagent (e.g., anaerobic antibody), with almost no contact with the air, to the reagent placement area of the microchip 10 of this embodiment will be described.

Figure 4:
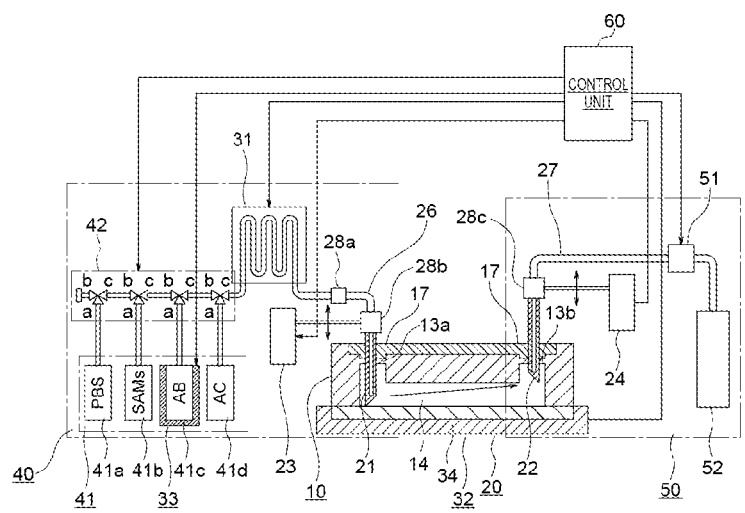
FIG. 4 shows an exemplary configuration of a reagent supplying apparatus to supply an anaerobic reagent into a channel of the microchip according to the embodiment of the present invention.
Figure 5:
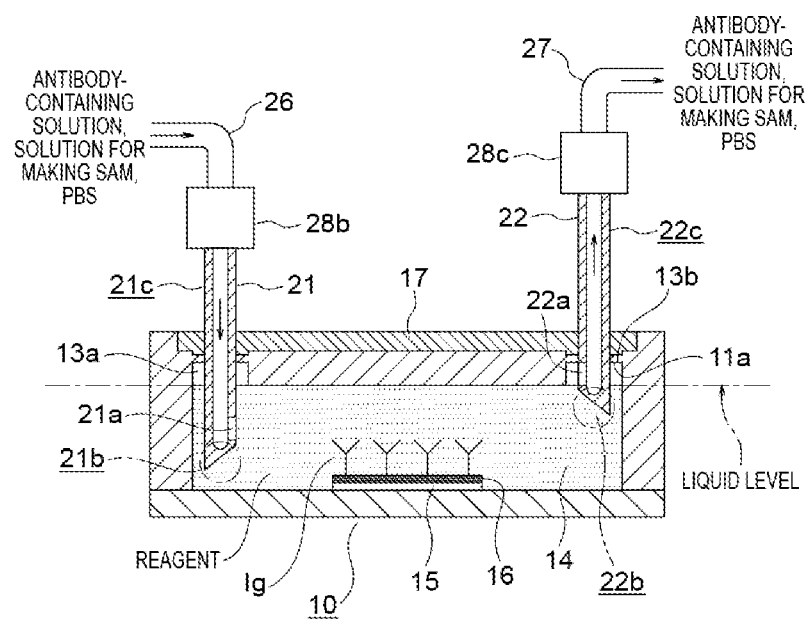
FIG. 5 is an enlarged view of a fluid releasing unit and a fluid recovering unit shown in FIG. 4.

FIGS. 4 and 5 show a block diagram that illustrates an exemplary configuration of the reagent supplying apparatus to supply the anaerobic reagent into the channel 14 of the microchip 10 of FIG. 1(a). The anaerobic antibody is used as the example of the anaerobic reagent here. The reagent supplying apparatus shown in FIG. 4 includes a reagent feeding mechanism 40, a test piece holding mechanism 20, a reagent recovery mechanism 50, and a control unit 60. FIG. 5 is an enlarged view that facilitates the understanding to the injection needle-like fluid releasing unit 21 and the injection needle-like fluid recovering unit 22 (will be described later).

I. Reagent Feeding Mechanism

As illustrated in FIG. 4, the reagent feeding mechanism 40 has the injection needle-like fluid releasing unit 21, a fluid releasing unit drive mechanism 23, a joint element 28b, a reagent solution feeding tube 26, another joint element 28a, a temperature control unit 31, a control valve unit 42, and a reagent reservoir unit 41.

The injection needle-like fluid releasing unit 21 is configured to penetrate the thin plate section 11a and the self-repairable sealing member 17 of the microchip 10 provided at the inlet 13a of the channel 14 of the microchip 10, and to release (introduce) the reagent into the channel 14 of the microchip 10. As depicted in FIG. 5, the injection needle-like fluid releasing unit 21 includes a hollow cylindrical member made from a stainless material. The free end 21b of the injection needle-like fluid releasing unit 21 is closed, and is shaped like a needle (e.g., bevel shape or slant shape similar to an injection needle). The opening 21a that communicates with the inner hollow space of the hollow cylindrical member and allows the reagent supplied from the inner hollow space to be released into the channel 14 is formed in the lateral face (cylindrical side wall) of the hollow cylindrical member at a position close (as close as possible) to the free end 21b. In the following description, the injection needle-like fluid releasing unit 21 is simply referred to as "fluid releasing unit 21."

Specifically, the free end (lower end) 21b of the fluid releasing unit 21 has a bevel shape like the injection needle, and therefore the fluid releasing unit 21 can easily penetrate the thin plate section 11a and the self-repairable sealing member 17 of the microchip. Because the free end 21b is closed, and the opening 21a is formed in the lateral face (side wall) of the cylindrical portion 21c of the hollow cylindrical member, chips are hardly generated from the self-repairable sealing member 17 when the fluid releasing unit 21 penetrates the self-repairable sealing member 17. In addition, the opening 21a will not be clogged by the chips of the self-repairable sealing member 17.

The fluid releasing unit 21 is driven (moved) up and down by the fluid releasing unit drive mechanism 23. Specifically, the fluid releasing unit drive mechanism 23 drives the fluid releasing unit 21 such that the opening 21a of the fluid releasing unit 21 penetrates the thin plate section 11a and the self-repairable sealing member 17 of the microchip 10 and enters the channel 14 of the microchip 10, and drives the fluid releasing unit 21 such that the fluid releasing unit 21 is completely removed from the microchip 10 through the thin plate section 11a and the self-repairable sealing member 17 of the microchip 10.

For example, the fluid releasing unit drive mechanism 23 is coupled to the joint member 28b, which connects the fluid releasing unit 21 to the reagent solution feeding tube 26. The reagent is conveyed through the reagent solution feeding tube 26.

One end of the reagent solution feeding tube 26 is connected to the fluid releasing unit 21 via the joint element 28b, as described above, and the other end thereof is connected to a piping that is temperature controlled by the temperature control unit 31. The temperature control unit 31 is provided for controlling the temperature of the reagent supplied from the reagent reservoir unit 41. Because the fluid releasing unit 21 and the joint element 28b are driven (moved) up and down by the fluid releasing unit drive mechanism 23, the reagent solution feeding tube 26 is made from a flexible tube that can move together with the fluid releasing unit 21 and the joint element 28b.

The reagent reservoir unit 41 stores the reagent that will be supplied to the channel 14 of the microchip 10. In the example shown in FIG. 4, the reagent reservoir unit 41 has a PBS reservoir 41a, an alkanthiol-containing solution reservoir 41b, an antibody-containing solution reservoir 41c, an antigen-containing solution reservoir 41d, and the temperature control unit 33.

In general, the antibody is stable when the antibody is reserved at a low temperature. Thus, the temperature of the antibody-containing solution reservoir 41c is controlled by the temperature control unit 33. The antibody is reserved at a temperature of, for example, 4 degrees C.

Each of the reservoirs of the reagent reservoir unit 41 is connected to the control valve unit 42 having a plurality of three-way valves. In the example shown in FIG. 4, the reagent reservoir unit 41 includes the four reservoirs, and therefore there are four piping for the reagent reservoir unit 41 and the control valve unit 42. The control valve unit 42 has a plurality of three-way electromagnetic valves or other types of valves. In FIG. 4, each of the three-way valves 42 (the control valves 42) has three ports a, b and c, and can switch between the passage a-c and the passage b-c. The passages b-c of the control valves 42 are connected like a manifold such that the four passages b-c of the four control valves 42 form a single passage. The port a of each control valve 42 is connected to the reagent reservoir unit 41. A stopcock or plug for the sealing is provided at the port b of that control valve 42 which is connected to the PBS reservoir 41a. The port c of that control valve 42 which is connected to the antigen-containing solution reservoir 41d is connected to the piping that is temperature controlled by the temperature control unit 31.

Specifically, as shown in FIG. 4, the four piping of the reagent reservoir unit 41 are ultimately integrated to a single piping, and is connected to the pipe that is temperature controlled by the temperature control unit 31. By controlling the switching (selection) of the passages by the associated control valves 42, it is possible to change (switch, select) the reagent to be released to the channel 14 of the microchip 10 from the fluid releasing unit 21 via the temperature control unit 31.

The temperature control unit 31 is provided for controlling the temperature of the reagent such as the antibody. Specifically, the temperature control unit 31 controls the temperature of the pipe connected to the single piping of the reagent reservoir unit 41. As mentioned above, the single piping of the reagent reservoir unit 41 is prepared by the four piping. One end of the pipe which is temperature controlled by the temperature control unit 31 is coupled to the reagent reservoir unit 41, as mentioned above. The other end of the pipe is coupled to the reagent solution feeding tube 26 via the joint element 28a.

II. Test Piece Holding Mechanism

As shown in FIG. 4, a test piece holding mechanism 20 has a temperature adjusting stage 34 equipped with a temperature control unit 32. The microchip 10 is put on the temperature adjusting (temperature-controlled) stage 34. The temperature adjusting stage 34 adjusts the temperature of the microchip 10. Specifically, the temperature of the microchip 10 placed on the temperature adjusting stage 34 is adjusted as the temperature of the temperature adjusting stage is controlled by the temperature control unit 32.

III. Reagent Recovery Mechanism

As shown in FIG. 4, the reagent recovery mechanism 50 includes the injection needle-like fluid recovering unit 22, the fluid recovering unit drive mechanism 24, the joint element 28c, the reagent solution discharge tube 27, a pump 51 and a drain tank (waste liquid tank) 52.

The injection needle-like fluid recovering unit 22 penetrates the self-repairable sealing member 17 located at the outlet 13b of the channel 14 of the microchip 10, and recovers into the drain tank 52 at least part of the reagent remaining in the channel 14 of the microchip 10. Similar to the fluid releasing unit 21, the injection needle-like fluid recovering unit 22 has a hollow cylindrical member, as shown in FIG. 5. The injection needle-like fluid recovering unit 22 is made from stainless. The free end (lower end) 22b of the fluid recovering unit 22 is closed, and has a shape similar to a needle (e.g., bevel shape or slant shape similar to an injection needle). An opening 22a that communicates with the inside hollow of the hollow cylindrical member and releases the reagent supplied from the inside hollow into the fluid is formed in the cylindrical side wall of the cylinder portion 22c of the hollow cylindrical member at a position close (as close as possible) to the free end 22b. In the following description, the injection needle-like fluid recovering unit 22 is simply referred to as the "fluid recovering unit 22."

As such, the free end 22b of the fluid recovering unit 22 has a bevel shape which is similar to an injection needle, and therefore the fluid recovering unit 22 can easily penetrate the thin plate section 11a and the self-repairable sealing member 17 of the microchip 10. In addition, because the free end 22b is closed and the opening 22a is formed in the side wall of the cylinder portion 22c of the hollow cylindrical member, chips are hardly generated from the self-repairable sealing member 17 when the fluid recovering unit 22 penetrates the self-repairable sealing member 17. The opening 22a will not be clogged by the chips of the self-repairable sealing member 17.

The fluid recovering unit 22 is moved upward and downward by the fluid recovering unit drive mechanism 24. Specifically, the fluid recovering unit drive mechanism 24 drives the fluid recovering unit 22 such that the opening 22a of the fluid recovering unit 22 penetrates the thin plate section 11a and the self-repairable sealing member 17 of the microchip 10 and enters the channel 14 of the microchip 10, and such that the fluid recovering unit 22 are completely removed from the microchip 10 through the thin plate section 11a and the self-repairable sealing member 17 of the microchip 10.

The fluid recovering unit drive mechanism 24 is connected to, for example, the joint element 28c, which connects the fluid recovering unit 22 to the reagent solution discharge tube 27. At least part of the reagent in the channel 14 is conveyed to the drain tank 52 through the reagent solution discharge tube 27.

The reagent solution discharge tube 27 is connected to the fluid recovering unit 22 via the joint element 28c at its one end and connected to the pump 51 at the other end, as described above. Because the fluid recovering unit 22 and the joint element 28c are moved upward and downward by the fluid recovering unit drive mechanism 24, the reagent solution discharge tube 27 is made from a flexible pipe in order to take the corresponding movement with the fluid recovering unit 22 and the joint element 28c.

As described above, the pump 51 feeds the reagent into the channel 14 of the microchip via the fluid releasing unit 21 from the reagent reservoir unit 41. The pump 51 also conveys at least part of the reagent to the drain tank 52 from the channel 14. The reagent (waste liquid) transported by the pump 51 is stored in the drain tank 52.

IV. Control Unit

The control unit 60 controls the fluid releasing unit drive mechanism 23, which belongs to the reagent feeding mechanism 40, the temperature control unit 31, the control valves 42, the temperature control unit 33, the temperature control unit 32 of the test piece holding mechanism 20, the fluid recovering unit drive mechanism 24, which belongs to the reagent recovery mechanism 50, and the pump 51.

V. Procedure for Fixing the Antibody in the Microchip Channel

The antibody is fixed in the microchip channel 14 shown in FIG. 1 in the following procedure, for example. This fixing procedure will be described with reference to FIGS. 4, 5, 6, 7 and 8.

(1) Arranging the Injection Needle-Like Fluid Releasing Unit and the Injection Needle-Like Fluid Recovering Unit in the Microchip The microchip 10, which is the test piece, is placed on the temperature adjusting stage 34. It should be noted that the microchip 10 may be put on the temperature adjusting stage 34 by an operator, or by a known conveyance mechanism (not shown). When the conveyance mechanism is used, the conveyance mechanism may be controlled by the control unit 60.

Before the microchip 10 is put on the temperature adjusting stage 34, the temperature control unit 32 of the temperature adjusting stage 34 performs the control in accordance with a command from the control unit 60 such that the temperature of the temperature adjusting stage 34 becomes a predetermined temperature, for example, 25-37 degrees C.

Likewise, the temperature control unit 31 shown in FIG. 4 performs, in advance, the control in accordance with a command from the control unit 60 such that the temperature of the pipe of the control unit 31 becomes a prescribed temperature, for example, 25-37 degrees C.

Figure 6A:
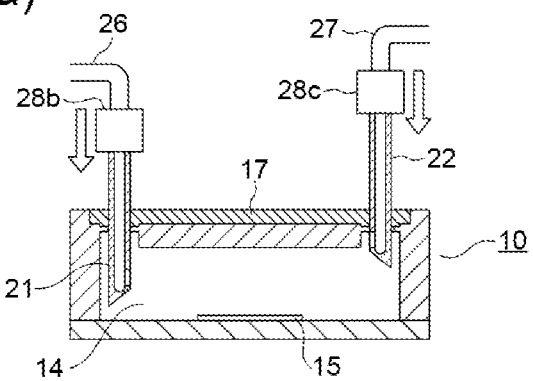
FIG. 6(a) to FIG. 6(c) are a first set of views useful to describe a procedure to fix an antibody in the microchip channel according to the embodiment of the present invention.
Figure 6B:
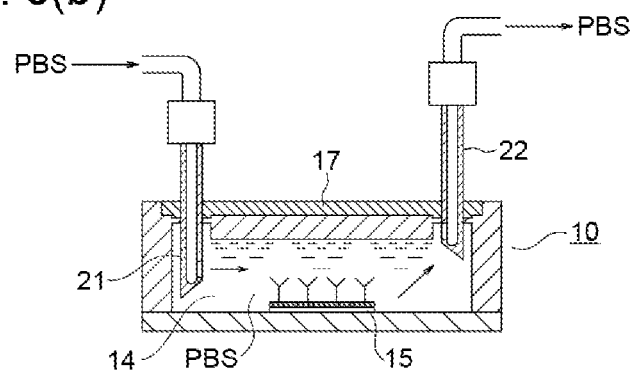
Figure 6C:
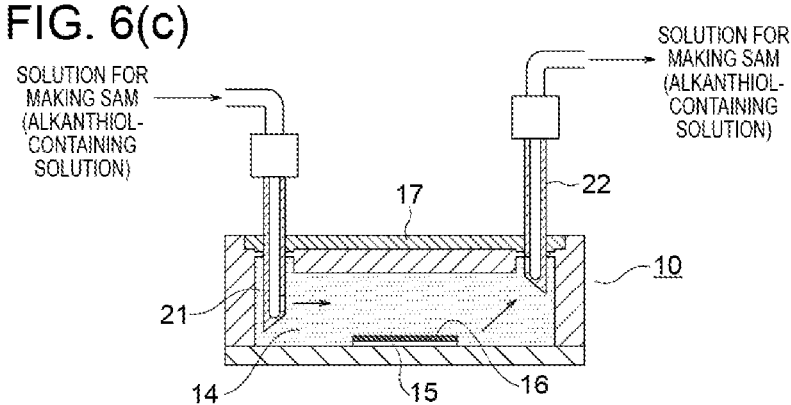

In response to the command from the control unit 60, the fluid releasing unit drive mechanism 23 moves the fluid releasing unit 21 (injection needle-like fluid releasing unit) downward to a predetermined position. As illustrated in FIG. 6(*a*), this movement causes the opening 21*a* of the fluid releasing unit 21 to penetrate the self-repairable sealing member 17 disposed at the inlet 13*a* of the microchip 10 and enter the channel 14 of the microchip 10. The predetermined position is a position at which the free end (lower end) of the fluid releasing unit 21 does not contact the second microchip base plate 12 of the microchip 10.

Likewise, in response to the command from the control unit 60, the fluid recovering unit drive mechanism 24 moves the fluid recovering unit 22 (injection needle-like fluid recovering unit) downward to a predetermined position. As illustrated in FIG. 6(*a*), this movement causes the opening 22*a* of the fluid recovering unit 22 to penetrate the thin plate section 11*a* and the self-repairable sealing member 17 at the outlet 13*b* of the microchip 10 and enter the channel 14 of the microchip. The predetermined position is a position at which the free end (lower end) of the fluid recovering unit 22 does not contact the second microchip base plate 12 of the microchip 10.

The control unit 60 moves and fixes the fluid releasing unit 21 and the fluid recovering unit 22 such that the position of the lower end of the opening 22*a* of the fluid recovering unit 22 is situated above the position of the upper end of the opening 21*a* of the fluid releasing unit 21.

The opening 21*a* of the fluid releasing unit 21 is arranged to face the opening 22*a* of the fluid recovering unit 22.

(2) Cleaning the Channel Interior with the PBS

In FIG. 4, it should be assumed that the passages b-c of the respective control valves 42 are selected.

The control unit 60 operates that control valve 42, among the four control valves 42, which is disposed on the piping extending from the PBS reservoir 41*a* (referred to as "PBS piping" hereinafter) to switch to the passage a-c (switching from the passage b-c to the passage a-c).

Subsequently, the control unit 60 starts activating the pump 51. Firstly, the air in the channel 14 of the microchip 10 is sucked from the opening 22*a* of the fluid recovering unit 22. Then, the PBS stored in the PBS reservoir 41*a* flows through the passage a-c of that control valve 42 which belongs to the PBS piping, the passages b-c of the remaining control valves 42, the temperature control unit 31 and the reagent solution feeding tube 26, and enters the channel 14 of the microchip 10 via the opening 21*a* of the fluid releasing unit 21. When the liquid level (liquid surface) of the PBS flowing in the channel 14 reaches the opening 22*a* of the fluid recovering unit 22, the PBD is sucked from the opening 22*a* of the fluid recovering unit 22 and sent to the drain tank 52 through the reagent solution discharge pipe 27.

The above-described procedure causes the PBS, which is fed into the channel 14 of the microchip from the opening 21*a* of the fluid releasing unit 21, to flow in the channel 14 and clean the channel 14, as shown in FIG. 6(*b*). Then, the PBS is discharged out of the channel 14 through the opening 22*a* of the fluid recovering unit 22 and sent to the waste liquid container 52. In other words, there is generated a flow of the PBS in the channel that cleans the interior of the channel.

The position of the lower end of the opening 22*a* of the fluid recovering unit 22 is decided (set) to be higher than the position of the upper end of the opening 21*a* of the fluid releasing unit 21. As depicted in FIG. 5, therefore, the liquid level of the PBS flowing in the channel 14 takes the position of the lower end of the opening 22*a* of the fluid recovering unit 22.

(3) Forming the SAM Film

After the cleaning is performed for a prescribed time, the control unit 60 selects the passage b-c of that control valve 42, among the four control valves 42, which belongs to the PBS piping (switching from the passage a-c to the passage b-c). The control unit 60 also selects the passage a-c of that control valve 42 which belongs to the piping extending from the alkanthiol-containing solution reservoir 41*b* (referred to as "SAMs piping" hereinafter) (switching from the passage b-c to the passage a-c). The alkanthiol-containing solution is the solution for forming the SAM, and the alkanthiol-containing solution is stored in the alkanthiol-containing solution reservoir 41*b*.

It should be noted that the time to be spent for cleaning with the PBS (the above-mentioned "prescribed time"), the timing for switching the passage of the control valve 42 associated with the PBS piping, and the timing for switching the passage of the control valve 42 associated with the SAMs piping are stored in advance in the control unit 60.

The above-described passage switching (selection) allows the PBS remaining in the channel 14 of the microchip to be sucked through the opening 22*a* of the fluid recovering unit 22, and allows the alkanthiol-containing solution stored in the alkanthiol-containing solution reservoir 41*b* to flow in the channel 14 of the microchip 10 from the opening 21*a* of the fluid releasing unit 21 via the passage a-c of the control valve 42 associated with the SAMs piping, the passage b-c of the control valve 42 associated with the piping extending from the antibody-containing reservoir 41*c* (referred to as "AB piping" hereinafter), the passage b-c of the control valve 42 associated with the piping extending from the antigen-containing solution reservoir 41*d* (referred to as "AC piping" hereinafter), the temperature control unit 31, and the reagent solution feeding tube 26. The port b of that control valve 42 which connects to the PBS reservoir 41*a* is sealed by a sealing plug, and therefore the alkanthiol-containing solution does not flow in the passage b-c of the control valve 42 associated with the PBS piping.

The above-described procedure firstly causes the alkanthiol-containing solution, which is fed in the channel 14 of the microchip from the opening 21*a* of the fluid releasing unit 21, to flow through the channel 14 while mixing with the PBS remaining in the channel 14, which is the residual PBS prior to the introduction of the alkanthiol-containing solution, as shown in FIG. 6(*c*). Then, the alkanthiol-containing solution is discharged out of the channel 14 through the opening 22*a* of the fluid recovering unit 22, and sent to the waste liquid tank 52. Then, the PBS concentration gradually decreases. Ultimately, the flow that almost only contains the alkanthiol-containing solution is generated in the channel 14. The alkanthiol contained in the alkanthiol-containing solution reacts with the Au thin film, and forms a SAM film (Self-Assembled Monolayer) on the Au thin film.

Because the position of the lower end of the opening 22*a* of the fluid recovering unit 22 is arranged to be higher than the position of the upper end of the opening 21*a* of the fluid releasing unit 21, the liquid level of the alkanthiol-containing solution flowing in the channel 14 is the position of the lower end of the opening 22*a* of the fluid recovering unit 22, as shown in FIG. 5.

(4) Cleaning the Channel Interior with the PBS

After a certain time elapses and the SAM film 16 is formed on the Au film, then the control unit 60 selects the passage b-c of that control valve 42, among the four control valves 42, which is associated with the SAMs piping. The control unit 60 also selects the passage a-c of that control valve 42 which is associated with the PBS piping.

It should be noted that the time for the alkanthiol-containing solution to flow through the channel 14 of the microchip until the SAM film 16 is formed on the Au film (the above-mentioned "certain time"), the timing for switching the passage of the control valve 42 associated with the SAMs piping, and the timing for switching the passage of the control valve 42 associated with the PBS piping are stored in advance in the control unit 60.

The above-described passage switching (selection) allows the alkanthiol-containing solution, which remains in the channel 14 of the microchip, to be sucked through the opening 22a of the fluid recovering unit 22, and allows the PBS to flow in the channel 14 of the microchip from the opening 21a of the fluid releasing unit 21 via the passage a-c of the control valve 42 associated with the PBS piping, the passages b-c of the remaining control valves 42, the temperature control unit 31 and the reagent solution feeding tube 26.

Figure 7D:
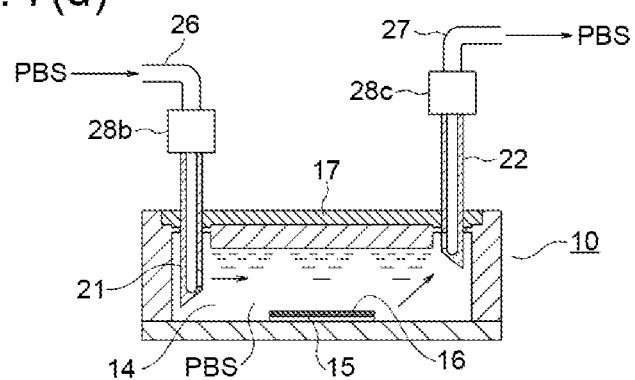
FIG. 7(d) to FIG. 7(f) are a second set of views useful to describe the procedure to fix the antibody in the microchip channel according to the embodiment of the present invention.

The above-described procedure firstly allows the PBS, which is fed to the channel 14 of the microchip from the opening 21a of the fluid releasing unit 21, to flow through the channel 14 and mix with the alkanthiol-containing solution remaining in the channel 14, as shown in FIG. 7(d). This procedure also causes the PBS to be discharged out of the channel 14 through the opening 22a of the fluid recovering unit and to be sent to the waste liquid tank 52. Then, the concentration of the alkanthiol-containing solution decreases gradually. Ultimately, the flow that almost only contains the PBS is generated in the channel 14. In this manner, the alkanthiol-containing solution that does not contribute to the formation of the SAM film 16 is expelled to the outside through the reagent solution discharge tube 27 together with the PBS.

Because the position of the lower end of the opening 22a of the fluid recovering unit 22 is set to be higher than the position of the upper end of the opening 21a of the fluid releasing unit 21, the liquid level of the PBS flowing in (through) the channel 14 is the position of the lower end of the opening 22a of the fluid recovering unit 22, as shown in FIG. 5.

(5) Fixing the Antibody

After the cleaning is performed for a prescribed time, the control unit 60 selects the passage b-c of the control valve 42 associated with the PBS piping, among the four control valves 42, and selects the passage a-c of that control valve 42 which is associated with the piping (AB piping) extending from the antibody-containing solution reservoir 41c. The antibody-containing solution is reserved in the antibody-containing solution reservoir 41c.

It should be noted that the time for cleaning with the PBS (the above-mentioned "prescribed time"), the timing for switching the passage of the control valve 42 associated with the PBS piping, and the timing for switching the passage of the control valve 42 associated with the AB piping are stored in advance in the control unit 60.

The above-described passage switching (selection) allows the PBS, which remains in the channel 14 of the microchip, to be sucked through the opening 22a of the fluid recovering unit 22, and allows the antibody-containing solution to flow in the channel 14 of the microchip from the opening 21a of the fluid releasing unit 21 via the passage a-c of the control valve 42 associated with the AB piping, the passage b-c of the control valve 42 associated with the AB piping extending from the antibody-containing solution reservoir 41c, the temperature control unit 31 and the reagent solution feeding tube 26.

The port b of that control valve 42 which connects to the PBS reservoir 41a is sealed by a sealing plug, and therefore the antibody-containing solution does not flow in the passage b-c of the control valve 42 associated with the SAMs piping and in the passage b-c of the control valve 42 associated with the PBS piping.

The antibody-containing solution, which is stored at a low temperature (e.g., 4 degrees C.) in the antibody-containing solution reservoir 41c, is heated to 25-37 degrees C. as the antibody-containing solution flows through the pipe of the temperature control unit 31, which is temperature controlled by the temperature control unit 31 shown in FIG. 4.

As described above, the temperature of the microchip 10 placed on the temperature adjusting stage 34 is maintained to, for example, 25-37 degrees C. by the temperature adjusting stage 34 which is temperature controlled by the temperature control unit 32. Therefore, the temperature of the antibody-containing solution flowing in the channel 14 of the microchip does not drop.

Figure 7E:
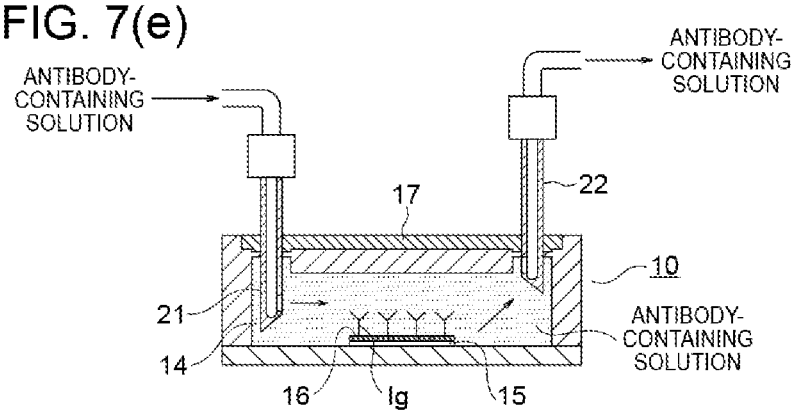

The above-described procedure firstly allows the antibody-containing solution, which is fed to the channel 14 of the microchip from the opening 21a of the fluid releasing unit 21, to flow through the channel 14 and mix with the PBS remaining in the channel 14 prior to the introduction of the antibody-containing solution, as shown in FIG. 7(e). This procedure also causes the antibody-containing solution to be discharged out of the channel 14 through the opening 22a of the fluid recovering unit 22 and to be sent to the waste liquid tank 52. Then, the concentration of the PBS decreases gradually. Ultimately, the flow that almost only contains the antibody-containing solution is generated in the channel 14. The antibody contained in the antibody-containing solution reacts with the alkanthiol SAM film 16 and chemically joins with the SAM film 16. Thus, the antibody is fixed on the SAM film 16. In other word, the antibody Ig is fixed on the metallic thin film 15.

Because the position of the lower end of the opening 22a of the fluid recovering unit 22 is set to be higher than the position of the upper end of the opening 21a of the fluid releasing unit 21, the liquid level of the antibody-containing solution flowing in (through) the channel 14 is the position of the lower end of the opening 22a of the fluid recovering unit 22, as shown in FIG. 5.

The position of the lower end of the opening 22a of the fluid recovering unit 22 is set such that the above-mentioned liquid level becomes the height that completely immerses the antibody Ig fixed on the SAM film 16 in the antibody-containing solution. As such, the antibody Ig fixed on the SAM film 16 does not contact the air.

Because the opening 21a of the fluid releasing unit 21 is formed in the cylindrical portion side wall of the hollow cylindrical member, as described above, the reagent supplied from the fluid releasing unit 21 (i.e., antibody-containing solution in this embodiment) is released from the opening in the direction perpendicular to the axial direction of the hollow cylindrical member. Thus, the reagent is released (introduced) laterally in FIGS. 5, 6 and 7.

As described above, the opening 21a of the fluid releasing unit 21 faces the opening 22a of the fluid recovering unit 22. Also, the position of the opening 21a of the fluid releasing unit is decided such that the antibody-containing solution released from the opening 21a in the lateral direction does not directly collide with the corner of the channel. Therefore, it is possible to suppress a chance for the antibody-containing solution flowing in the channel 14 to become a turbulent flow.

In summary, the arrangement (setting) of the fluid releasing unit 21 and the fluid recovering unit 22 in accordance with the procedure (1) causes the lower end of the opening 22a of the fluid recovering unit 22 to take the above-mentioned position and also causes the opening 21a of the fluid releasing unit 21 to take the above-mentioned position respectively.

(6) Cleaning the Channel Interior with the PBS

After a certain time elapses and the antibody Ig is fixed on the SAM film 16, the control unit 60 selects the passage b-c of that control valve 42, among the four control valves 42, which is associated with the AB piping. The control unit 60 also selects the passage a-c of that control valve 42 which is associated with the PBS piping.

It should be noted that the time for the antibody-containing solution to flow through the channel 14 of the microchip until the antibody Ig is fixed on the SAM film 16 (the above-mentioned "certain time"), the timing for switching the passage of the control valve 42 associated with the AB piping, and the timing for switching the passage of the control valve 42 associated with the PBS piping are stored in advance in the control unit 60.

The above-described passage switching (selection) allows the alkanthiol-containing solution, which remains in the channel 14 of the microchip, to be sucked through the opening 22a of the fluid recovering unit 22, and allows the PBS to flow in the channel 14 of the microchip from the opening 21a of the fluid releasing unit 21 via the passage a-c of the control valve 42 associated with the PBS piping, the passages b-c of the remaining control valves 42, the temperature control unit 31 and the reagent solution feeding tube 26.

Figure 7F:
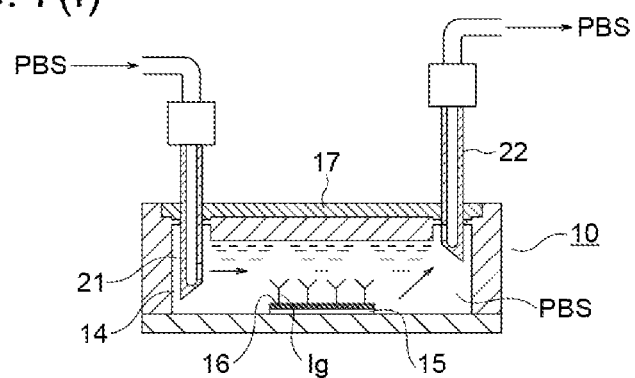

The above-described procedure allows the antibody Ig, which remains on the surface of the antibody Ig fixed on the SAM film 16 but is not fixed, and the antibody Ig remaining in a region other than the SAM film 16 to be discharged to the outside through the reagent solution discharge tube 27 together with the PBS, as shown in FIG. 7(f).

Because the position of the lower end of the opening 22a of the fluid recovering unit 22 is set to be higher than the position of the upper end of the opening 21a of the fluid releasing unit 21, the liquid level of the PBS flowing in (through) the channel 14 is the position of the lower end of the opening 22a of the fluid recovering unit 22, as shown in FIG. 5. This liquid level is a height that completely immerses the antibody Ig fixed on the SAM film 16 in the PBS. Therefore, the antibody Ig fixed on the SAM film 16 does not contact the air.

The above-described procedures (1) to (6) allow the antibody Ig to be fixed in the reagent placement area of the channel 14 of the microchip (i.e., SAM film forming area on the metallic thin film 15)

As understood from the above-described procedures, the metallic thin film 15 is always immersed in the PBS, the SAM film forming solution (alkanthiol-containing solution in this embodiment) or the antibody-containing solution after the interior of the channel 14 is cleaned with the PBS in the procedure (2). The SAM film formation is carried out in the procedure (3) while the metallic thin film 15 is in no contact with the air. The antibody is fixed on the SAM film 16 in the procedure (5) while the antibody Ig does not contact the air under the condition that no air remains in (on) the SAM film 16. The antibody Ig, which is not fixed on the SAM film 16, is discharged in the procedure (6) while the antibody Ig fixed on the SAM film 16 does not contact the air.

This is because, as described above, the position of the lower end of the opening 22a of the fluid recovering unit 22 is set such that the liquid level of the reagent flowing in the channel 14 is the height that can completely immerse the antibody Ig fixed on the SAM film 16 in the reagent.

Therefore, the reagent supplying apparatus that uses the microchip 10 of this embodiment can supply the anaerobic reagent such as the anaerobic antibody to the reagent placement area of the microchip 10 with no contact with the air. In other words, it is possible to fix the anaerobic antibody in the reagent placement area of the microchip 10 without making the anaerobic antibody inactive.

Because the reagent is mechanically (automatically) supplied to the channel 14 of the microchip 10 by the control unit 60, the reagent feeding mechanism 40, and the reagent recovering mechanism 50, it is possible to feed the reagent to the channel 14 of the microchip 10 stably without irregularities.

The opening 21a of the fluid releasing unit 21 faces the opening 22a of the fluid recovering unit 22, and the opening 21a of the fluid releasing unit 21 takes the position that avoids the direct collision of the antibody-containing solution, which is released (introduced) from the opening in the lateral direction, onto the corner of the channel 14. Therefore, it is possible to reduce a chance for the antibody-containing solution flowing in the channel 14 to become a turbulent flow. Accordingly, the contact between the antibody Ig contained in the antibody-containing solution and the alkanthiol SAM film 16 is hardly disordered (distorted), and the reaction of the antibody Ig with the SAM film 16 proceeds in a favorable manner. Thus, it is possible to fix the antibody Ig on the SAM film 16 in a stable manner.

The inlet 13a and the outlet 13b of the channel 14 of the microchip 10 according to this embodiment are sealed by the self-repairable (self-repairing) sealing member 17, which is for example made from a silicone gel. Thus, even when the fluid releasing unit 21 and the fluid recovering unit 22 of the reagent supplying apparatus according to this embodiment penetrate the thin plate sections 11a and the self-repairable sealing member 17 of the microchip and reach the reagent placement area, the close contact at the interface between the self-repairable sealing member 17 and the fluid releasing unit 21 and at the interface between the self-repairable sealing member 17 and the fluid recovering unit 22 is maintained favorably because the self-repairable sealing member 17 deforms upon application of a force and returns to an original shape (shape before application of the force) upon release of the applied force. Accordingly, the outside air hardly enters the reagent placement area, which is the closed space, through these interfaces.

VI. Procedure for Causing the Antibody-Antigen Reaction in the Microchip Channel After the antibody is fixed in the microchip 10, the following procedure takes place to feed an antigen to the fixed antibody Ig so as to trigger an antibody-antigen reaction.

(7) Antibody-Antigen Reaction

After the cleaning is carried out for a prescribed time in the procedure (6), the control unit 60 selects the passage b-c of that control valve 42 which is associated with the PBS piping, among the four control valves 42, and selects the passage a-c of that control valve 42 which is associated with the AC piping extending from the antigen-containing solution reservoir 41*d*. The antigen-containing solution is stored in the antigen-containing solution reservoir 41*d*.

It should be noted that the time for cleaning with the PBS (the above-mentioned "prescribed time"), the timing for selecting (switching) the passage of the control valve 42 associated with the PBS piping, and the timing for selecting (switching) the passage of the control valve 42 associated with the AC piping are stored in advance in the control unit 60.

The above-described passage switching (selection) allows the PBS, which remains in the channel 14 of the microchip 10, to be sucked through the opening 22*a* of the fluid recovering unit 22, and allows the antigen-containing solution to flow in the channel 14 of the microchip from the opening 21*a* of the fluid releasing unit 21 via the passage a-c of the control valve 42 associated with the AC piping, the temperature control unit 31 and the reagent solution feeding tube 26. The port b of that control valve 42 which connects to the PBS reservoir 41*a* is sealed by the sealing plug, and therefore the antigen-containing solution does not flow in the passage b-c of that control valve 42 which is associated with the AB piping, the passage b-c of that control valve 42 which is associated with the SAMs piping, and the passage b-c of that control valve 42 which is associated with the PBS piping.

The antigen-containing solution is heated to, for example, 25-37 degrees C. as the antigen-containing solution flows through the pipe of the temperature control unit 31, which is temperature controlled by the temperature control unit 31 shown in FIG. 4.

Figure 8G:
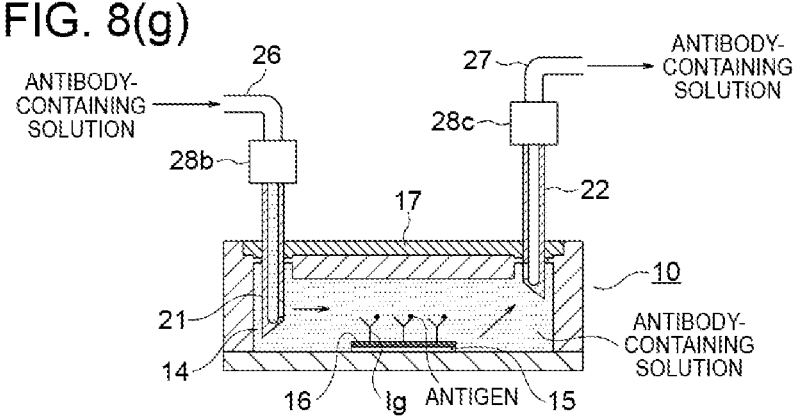
FIG. 8(g) and FIG. 8(i) are a third set of views useful to describe the procedure to fix the antibody in the microchip channel according to the embodiment of the present invention.
Figure 8H:
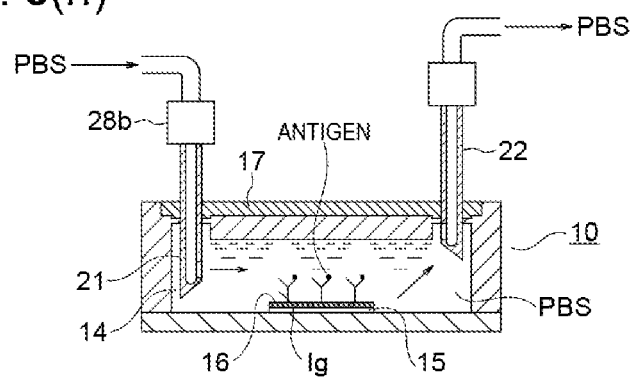

The above-described procedure firstly allows the antigen-containing solution, which is fed to the channel 14 of the microchip from the opening 21*a* of the fluid releasing unit 21, to flow through the channel 14 and mix with the PBS remaining in the channel 14 prior to the introduction of the antigen-containing solution, as shown in FIG. 8(*g*). This procedure also causes the antigen-containing solution to be discharged out of the channel 14 through the opening 22*a* of the fluid recovering unit 22 and to be sent to the waste liquid tank 52. Then, the concentration of the PBS decreases gradually. Ultimately, the flow that almost only contains the antigen-containing solution is generated in the channel 14. The antigen contained in the antigen-containing solution reacts with the antibody Ig fixed on the SAM film 16 (i.e., antibody-antigen reaction takes place), and chemically joins with the antibody. As described above, the antibody-antigen reaction takes place in the antigen-containing solution without the air because the fluid releasing unit 21 and the fluid recovering unit 22 are arranged in accordance with the procedure (1).

As described above, the temperature of the microchip 10 placed on the temperature adjusting stage 34 is maintained at, for example, 25-37 degrees C. by the temperature adjusting stage 34 which is temperature controlled by the temperature control unit 32. Therefore, the antibody-antigen reaction takes place in the microchip channel 14 at a temperature of 25-37 degrees C. (under the temperature condition of 25-37 degrees C.). This temperature condition (temperature range) is similar to a human body temperature.

(8) Cleaning the Channel Interior with the PBS

After a certain time elapses and the antibody-antigen reaction is completed, the control unit 60 selects the passage b-c of that control valve 42, among the four control valves 42, which is associated with the AC piping and also selects the passage a-c of that control valve 42 which is associated with the PBS piping.

It should be noted that the time for the antigen-containing solution to flow in the channel 14 of the microchip until the antibody-antigen reaction is completed (the above-mentioned "certain time"), the timing for selecting (switching) the passage of the control valve 42 associated with the AC piping, and the timing for selecting (switching) the passage of the control valve 42 associated with the PBS piping are stored in advance in the control unit 60.

The above-described passage switching (selection) allows the antigen-containing solution, which remains in the channel 14 of the microchip 10, to be sucked through the opening 22*a* of the fluid recovering unit 22, and allows the PBS to flow in the channel 14 of the microchip from the opening 21*a* of the fluid releasing unit 21 via the passage a-c of the control valve 42 associated with the PBS piping, the passages b-c of the remaining control valves 42, the temperature control unit 31 and the reagent solution feeding tube 26.

In this manner, the antigen, which does not contribute to the antibody-antigen reaction and remains in the channel, is expelled to the outside through the reagent solution discharge tube 27 together with the PBS, as shown in FIG. 8 (*h*).

The above-described procedures (7) and (8) cause the antigen to be supplied to the antibody Ig fixed in the microchip channel 14, and trigger the antibody-antigen reaction.

As obvious from the above-described procedures, the antibody-antigen reaction takes place in the procedure (7) while the antibody Ig fixed on the SAM film 16 does not contact the air. The antigen, which does not contribute to the antibody-antigen reaction and remains in the channel, is discharged in the procedure (8) without causing the antibody Ig to contact the air.

This is because the position of the lower end of the opening of the fluid recovering unit is decided (set) such that the liquid level of the reagent flowing in the channel takes the height that completely immerses the antibody Ig fixed on the SAM film 16 in the antibody-containing solution, as described above.

Therefore, the reagent supplying apparatus that uses the microchip 10 of this embodiment can supply the antigen to the reagent placement area of the microchip 10 while avoiding the contact between the antigen and the air. Consequently, it is possible to cause the antigen-antibody reaction to take place without deactivating the anaerobic antibody Ig fixed in the reagent placement area of the microchip 10.

Because the reagent is mechanically (automatically) fed to the channel 14 of the microchip by the control unit 60, the reagent feeding mechanism 40 and the reagent recovering mechanism 50, it is possible to feed the reagent to the channel 14 of the microchip stably without irregularities.

(9) Removing the Injection Needle-Like Fluid Releasing Unit and Injection Needle-Like Fluid Recovering Unit from the Microchip After the cleaning is carried out for a prescribed time, the control unit 60 selects the passage b-c of that control valve 42, among the four control valves 42, which is associated with the PBS piping. It should be noted that the time for cleaning with the PBS (the above-mentioned "prescribed time"), and the timing for selecting (switching) the passage of the control valve 42 associated with the PBS piping are stored in advance in the control unit 60.

Subsequently, the control unit 60 deactivates the pump 51. This stops the flow, which is almost only contains the PBS, in the microchip channel 14. As described above, because the position of the lower end of the opening of the fluid recovering unit 22 (injection needle-like fluid recovering unit) is arranged to be higher the position of the upper end of the opening of the fluid releasing unit 21 (injection needle-like fluid releasing unit), the liquid level of the PBS is at the position of the lower end of the opening 22a of the fluid recovering unit 22, as shown in FIG. 5.

Because the position of the lower end of the opening 22a of the fluid recovering unit 22 is set (decided) such that the liquid level has the height to entirely immerse, in the PBS, the antibody Ig fixed on the SAM film 16, the antibody Ig, which is fixed on the SAM film 16 and finishes the antibody-antigen reaction, does not contact the air.

Figure 8I:
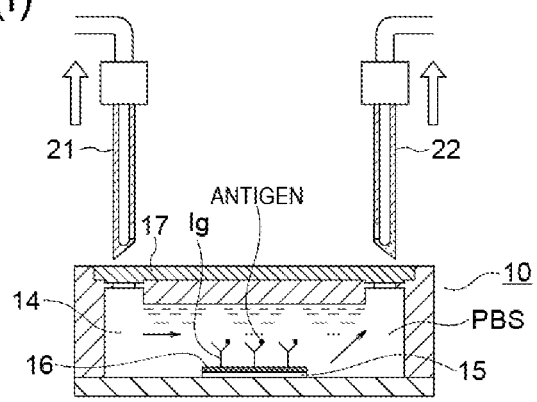
Figure 9A:
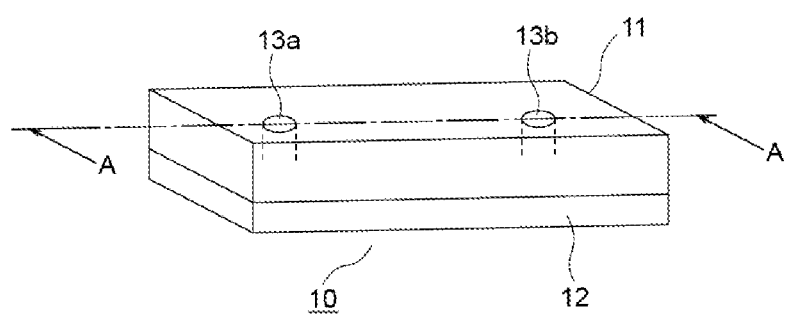
FIG. 9(a) is a schematic view showing a configuration of the microchip.
Figure 9B:
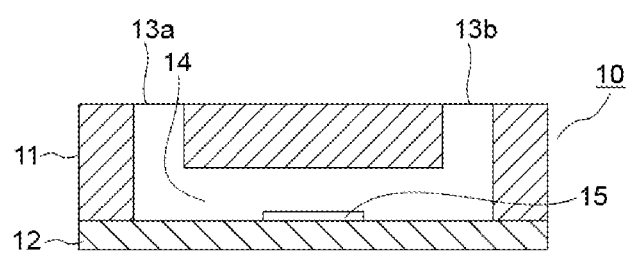
FIG. 9(b) is a cross-sectional view taken along the line A-A in FIG. 9(a).
Figure 10A:
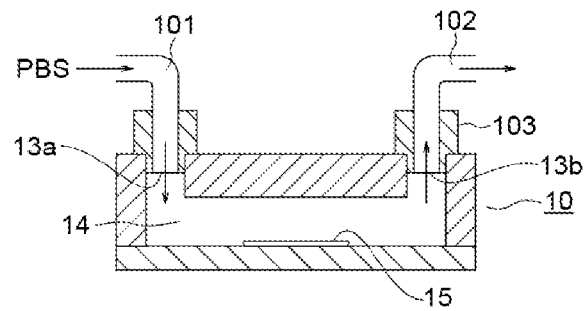
FIG. 10(a) to FIG. 10(c) are a first set of views useful to describe a procedure to fix an antibody in the channel of the conventional microchip.
Figure 10B:
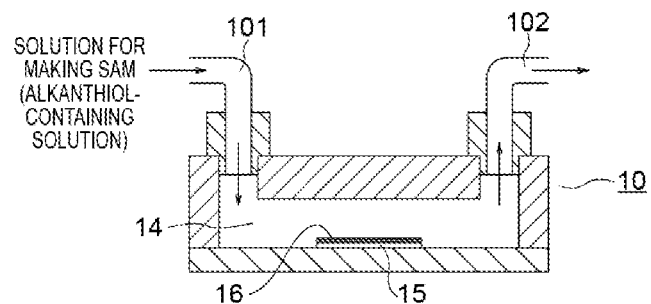
Figure 10C:
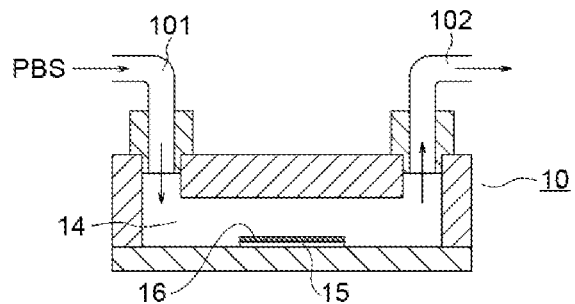
Figure 11D:
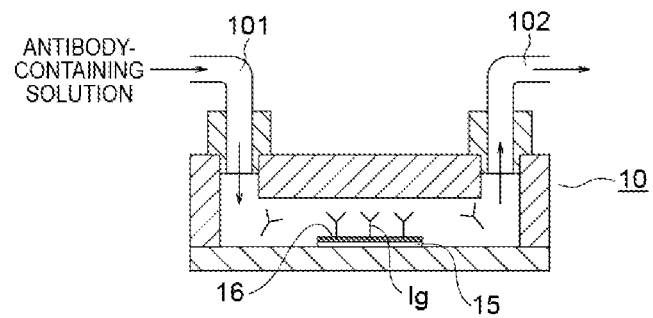
FIG. 11(d) to FIG. 11(f) are a second set of views useful to describe the procedure to fix the antibody in the channel of the conventional microchip.
Figure 11E:
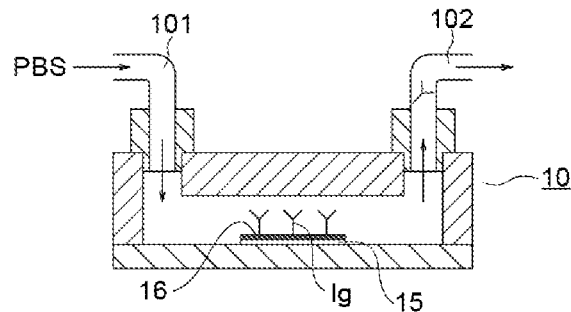
Figure 11F:
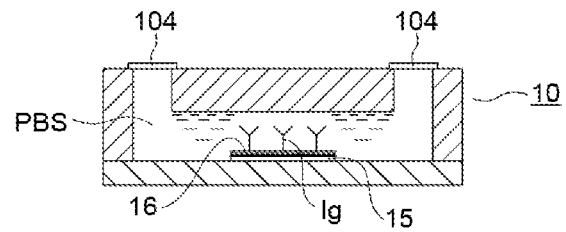
Figure 12:
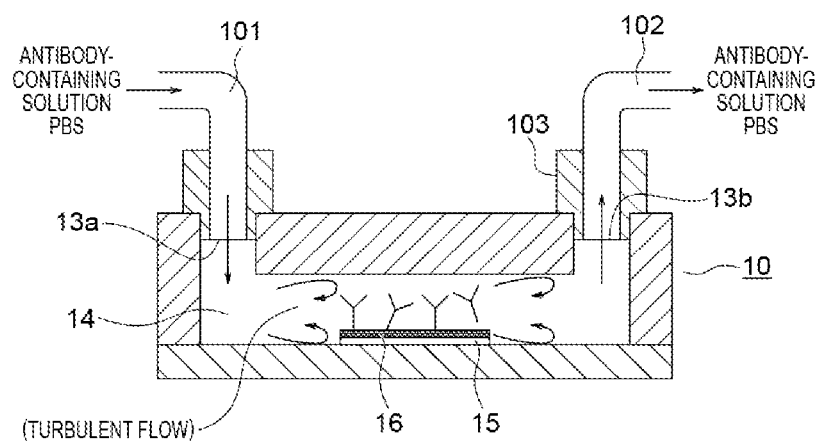
FIG. 12 illustrates how the contact between an antibody contained in an antibody-containing solution and a SAM film is disordered under an influence of a turbulent flow.

The fluid releasing unit drive mechanism 23 moves the fluid releasing unit 21 upward to a predetermined position in response to the command from the control unit 60. As illustrated in FIG. 8(i), this movement causes the opening 21a of the fluid releasing unit 21 to leave the channel 14 of the microchip (to be removed from the microchip channel 14). The predetermined position is a position that allows the fluid releasing unit 21 to completely leave the microchip 10 through the thin plate section 11a and the self-repairable sealing member 17 disposed at the inlet of the microchip 10.

Likewise, the fluid recovering unit drive mechanism 24 moves the fluid recovering unit 22 upward to a predetermined position in response to the command from the control unit 60. As illustrated in FIG. 8(i), this movement causes the opening 22a of the fluid recovering unit 22 to leave (to be removed from) the channel 14 of the microchip. The predetermined position is a position that allows the fluid recovering unit 22 to completely leave the microchip 10 through the thin plate section 11a and the self-repairable sealing member 17 disposed at the outlet 13b of the microchip 10.

Even if the fluid releasing unit 21 and the fluid recovering unit 22 that penetrate the thin plate sections 11a and the self-repairable sealing member 17 of the microchip 10 are removed through the thin plate sections 11a and the self-repairable sealing member 17, the self-repairable sealing member 17 deforms upon application of a force and returns to the original shape upon release of the applied force. Therefore, the openings created in the thin plate sections 11a by the fluid releasing unit 21 and the fluid recovering unit 22 that penetrate and leave the thin plate sections 11a and the self-repairable sealing member 17 remain, but the openings created in the self-repairable sealing member 17 are promptly closed. Consequently, even after the fluid releasing unit 21 and the fluid recovering unit 22 are removed from the thin plate sections 11a and the self-repairable sealing member 17 of the microchip, it is possible to prevent the air from entering the channel from the outside.

The microchip 10 placed on the temperature-controlled (temperature controlling) stage 34 is conveyed to a measuring device to measure the antibody-antigen reaction. It should be noted that the microchip 10 may be conveyed to the measuring device by an operator or a known conveying mechanism (not shown). If the conveying mechanism is employed, the conveying mechanism may be controlled by the control unit 60.

Figure 14:
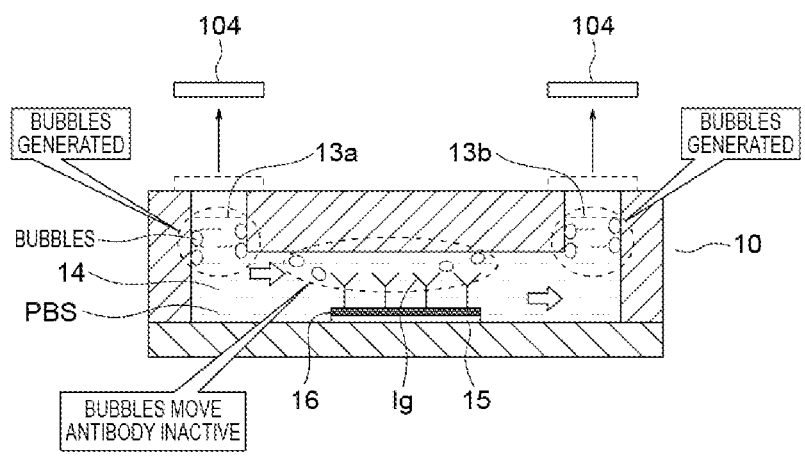
FIG. 14 is a view useful to describe how bubbles are generated when sealing members are removed from an inlet and an outlet.

If no subsequent fixing of the antibody or the like is carried out in the microchip 10, the temperature control unit 32 of the temperature-controlled stage 34 stops the temperature control to the temperature-controlled stage 34 in response to a command from the control unit 60. Likewise, the temperature control unit 31 shown in FIG. 14 stops the temperature control to the pipe of the temperature control unit 31 in response to a command from the control unit 60.

Although the foregoing deals with the example that automatically supplies the reagent to the microchip under the control of the control unit 60, part or entire of the above-described procedures and/or operations may be manually performed by a person.

REFERENCE SIGN LIST

10 Microchip
11 First microchip base plate
11a Thin plate section
11b Step portion
12 Second microchip base plate
13a Outlet
13b Inlet
14 Channel
15 Metallic thin film
16 SAM film
17 Self-repairable sealing member (adhesive gel)
20 Test piece holding mechanism
21 Injection needle-like fluid releasing unit
21a, 22a Opening
21b, 22b Free end
21c, 22c Cylindrical portion
22 Injection needle-like fluid recovering unit
23 Fluid releasing unit drive mechanism
24 Fluid recovering unit drive mechanism
26 Reagent solution feeding tube
27 Reagent solution discharge tube
28a Joint element
28b Joint element
28c Joint element
31 Temperature control unit
32 Temperature control unit
33 Temperature control unit
34 Temperature adjusting stage
40 Reagent feeding mechanism
41 Reagent reservoir unit
41a PBS reservoir
41b Alkanthiol-containing solution reservoir
41c Antibody-containing solution reservoir
41d Antigen-containing solution reservoir
42 Control valve
50 Reagent recovery mechanism
51 Pump
52 Drain tank
60 Control unit
71 First mold
72 Second mold
73 Silicone resin
Ig Antibody

The invention claimed is:

1. A system comprising a microchip and a reagent supplying apparatus for supplying a reagent to the microchip, the microchip comprising:
   a channel, which is a space having a reagent placement area therein;
   an inlet and an outlet which serve as openings of the channel; and
   a self-repairing sealing member that airtightly closes the inlet and the outlet of the channel;
the reagent supplying apparatus comprising:
   a fluid releasing unit that releases the reagent to the channel of the microchip and a fluid recovering unit that recovers the reagent released from the fluid releasing unit from the channel of the microchip; and a fluid releasing unit drive mechanism and a fluid recovering unit drive mechanism that independently move the fluid releasing unit and the fluid recovering unit up and down relatively with respect to each other to cause the fluid releasing unit and the fluid recovering unit to penetrate the self-repairing sealing member and to be removed from the channel of the microchip, respectively, each of the fluid releasing unit and the fluid recovering unit including a hollow cylindrical member, a free end of each said hollow cylindrical member being closed, the free end of each said hollow cylindrical member being shaped like a needle, and an opening formed in a cylindrical side wall of each said hollow cylindrical member to communicate with an inner hollow of each said hollow cylindrical member, each of the fluid releasing unit drive mechanism and the fluid recovering unit drive mechanism relatively positions the fluid releasing unit and the fluid recovering unit, respectively, such that a position of a lower end of the opening of the fluid recovering unit is situated above a position of an upper end of the opening of the fluid releasing unit in the channel of the microchip during the reagent being supplied, and each of the fluid releasing unit and the fluid recovering unit is engaged within the channel of the microchip at different depths of the channel, wherein the opening of the fluid releasing unit faces the opening of the fluid recovering unit.

2. The system comprising the microchip and the reagent supplying apparatus according to claim 1, wherein the fluid recovering unit successively feeds a plurality of kinds of reagent to the channel of the microchip from the inlet of the channel, and the fluid recovering unit discharges the reagents, which are successively fed to the channel, from the outlet of the channel.

3. The system comprising the microchip and the reagent supplying apparatus according to claim 1, wherein the self-repairing sealing member includes a silicone gel.

4. The system comprising the microchip and the reagent supplying apparatus according to claim 1 further including:
a reagent reservoir unit that reserves the reagent to be supplied to the fluid releasing unit; and
a first temperature controller connected between the reagent reservoir unit and the fluid releasing unit, wherein the first temperature controller controls a temperature of the reagent.

5. The system comprising the microchip and the reagent supplying apparatus according to claim 1 further including a temperature adjuster that is mounted to the microchip, and
a second temperature controller controlling a temperature of the temperature adjuster.

6. The system comprising the microchip and the reagent supplying apparatus according to claim 1, wherein the opening formed in the cylindrical side wall of each said hollow cylindrical member is situated in the vicinity of the free end of each said hollow cylindrical member.

7. The system comprising the microchip and the reagent supplying apparatus according to claim 1, the microchip including:
the channel having a bottom face on which a SAM film and an anaerobic antibody are to be formed; and
the openings serving as an inlet and an outlet to communicate with the channel.

8. The system comprising the microchip and the reagent supplying apparatus of claim 1, the reagent supplying apparatus further comprising:
a first control line connected to the fluid releasing unit drive mechanism;
a second control line independent of the first control line, the second control line connected to the fluid recovering unit drive mechanism;
a first support member provided between the fluid releasing unit drive mechanism and the fluid releasing unit; and
a second support member independent of the first support member, the second support member provided between the fluid recovering unit drive mechanism and the fluid recovering unit.

9. The system comprising the microchip and the reagent supplying apparatus of claim 1, wherein
the reagent includes an anaerobic antibody containing solution that contains an anaerobic antibody to be fixed in the reagent placement area, and
when the anaerobic antibody is fixed in the reagent placement area, the lower end of the opening of the fluid recovering unit is positioned so that a liquid level of the reagent supplied to the channel becomes a height that completely immerses the anaerobic antibody fixed in the reagent placement area.

10. The system comprising the microchip and the reagent supplying apparatus of claim 1, wherein the fluid releasing unit is positioned so that the reagent supplied from the fluid releasing unit is released from the opening of the fluid releasing unit in a direction perpendicular to an axial direction of the hollow cylindrical member.

11. The system comprising the microchip and the reagent supplying apparatus of claim 1, wherein the opening of the fluid releasing unit is positioned such that the reagent is released from the opening in a direction that does not directly collide with a corner of the channel.

12. A method of using the system of claim 1 to supply the reagent to the microchip from the reagent supplying apparatus the method comprising:
independently moving the fluid releasing unit and the fluid recovering unit up and down relatively with respect to each other;
causing the fluid releasing unit having the free end, which is shaped like the needle, and having the opening as a fluid release opening, and the fluid recovering unit having the free end, which is shaped like the needle, and having the opening as a fluid recovery opening, to penetrate the self-repairing member disposed at the inlet and the outlet respectively and enter the space having the reagent placement area such that the opening of the fluid releasing unit and the opening of the fluid recovering unit communicate with the space having the reagent placement area;
relatively positioning the fluid releasing unit and the fluid recovering unit such that the position of the lower end of the opening of the fluid recovering unit is situated above the position of the upper end of the opening of the fluid releasing unit in the channel of the microchip during the reagent being supplied;
feeding the reagent from the fluid releasing unit, and discharging the reagent through the fluid recovering unit to supply the reagent to the space having the reagent placement area; and removing, after feeding the reagent, the fluid releasing unit and the fluid recovering unit from the self-repairing sealing member.

\* \* \* \* \*